United States Patent [19]

Witte et al.

[11] Patent Number: 5,550,054
[45] Date of Patent: Aug. 27, 1996

[54] HEMATOPOIETIC RESTRICTED TYROSINE KINASE (BPK)

[75] Inventors: Owen Witte, Sherman Oaks; Satoshi Tsukada; Douglas Saffran, both of Los Angeles; David Rawlings, Santa Monica, all of Calif.

[73] Assignee: The Regents of the University of California, Oakland, Calif.

[21] Appl. No.: 391,615

[22] Filed: Feb. 21, 1995

Related U.S. Application Data

[63] Continuation of Ser. No. 6,449, Jan. 21, 1993, abandoned, which is a continuation-in-part of Ser. No. 985,998, Dec. 4, 1992, abandoned.

[51] Int. Cl.$^6$ .............. C12N 1/21; C12N 5/10; C12N 15/54; C12N 9/12
[52] U.S. Cl. .......... 435/240.2; 435/194; 435/172.3; 435/6; 435/252.3; 435/320.1; 435/69.1; 536/23.1; 536/23.2; 935/14; 935/27; 935/56; 935/66; 935/70; 935/72
[58] Field of Search ................ 536/23.1, 23.2; 435/194, 172.3, 240.2, 6, 252.3, 320.1, 69.1; 935/14, 27, 56, 72, 66, 70

[56] References Cited

PUBLICATIONS

D. Vetrie et al. Nature 361: 226–233 (Jan. 1993).
R. C. Allen et al. Hum. Mol. Genet. 1(3) 216 (1992).
Y. Yamanashi et al. Proc. Natl. Acad. Sci. 86: 6538–6542 (Sep. 1989).
I. P. Wicks et al. Proc. Natl. Acad. Sci. 89: 1611–1615 (Mar. 1992).
D. Kitamura et al. Nuc. Acids Res. 17(22) 9367–9379 (Nov. 1989).
S. M. Dymecki et al. Science 247: 332–336 (Jan. 1990).
D. A. Holtzman et al. Proc. Natl. Acad. Sci. 84: 8325–8329 (Dec. 1987).

*Primary Examiner*—Robert A. Wax
*Assistant Examiner*—Rebecca Prouty
*Attorney, Agent, or Firm*—Bertram I. Rowland

[57] ABSTRACT

Novel hematopoietic-restricted tyrosine kinases are provided, where the tyrosine kinases provide for autophosphorylation and transphosphorylation. Modulation of the activity of the subject compositions can be used to restrict growth and differentiation, to correct genetic deficiencies, and to elucidate the activation pathway involved with the subject tyrosine kinases. In addition, the tyrosine kinases may be used in a variety of assays as a label or in the production of the phosphorylated peptides.

6 Claims, 5 Drawing Sheets

```
  1  TAAGAATATGTCTCCAGGTCCAGAGTCTTCAGAGATCAAGTCCCACCTTCCAAGTCCTGG
 61  CATCTCACGACGTCTGGGGAGCTACCTGCATTAAGTCAGAACTGAGTACACAAACAAGTT
121  CCAGAGAGAGGAAGCCATGGCTGCAGTGATACTGGAGAGCATCTTTCTGAAGCGCTCCCA
                M  A  A  V  I  L  E  S  I  F  L  K  R  S  Q
181  GCAGAAAAAGAAAACATCACCTTTAAACTTCAAGAAGCGCCTGTTTCTCTTGACTGTACA
      Q  K  K  K  T  S  P  L  N  F  K  K  R  L  F  L  L  T  V  H
241  CAAACTTTCATACTATGAATATGACTTTGAACGTGGGAGAAGAGGCAGTAAGAAAGGTTC
      K  L  S  Y  Y  E  Y  D  F  E  R  G  R  R  G  S  K  K  G  S
301  AATAGATGTTGAGAAGATCACCTGTGTTGAAACAGTAATTCCTGAAAAAAATCCCCCACC
      I  D  V  E  K  I  T  C  V  E  T  V  I  P  E  K  N  P  P  P
361  AGAAAGACAGATTCCGAGGAGAGGTGAGGAGTCTAGTGAAATGGAACAGATTTCAATCAT
      E  R  Q  I  P  R  R  G  E  E  S  S  E  M  E  Q  I  S  I  I
421  TGAAAGGTTCCCGTACCCATTCCAGGTTGTATATGATGAAGGACCTCTCTATGTTTTCTC
      E  R  F  P  Y  P  F  Q  V  V  Y  D  E  G  P  L  Y  V  F  S
481  CCCAACTGAAGAGCTGAGAAAGCCGTGGATTCACCAGCTCAAAAATGTAATCCGGTACAA
      P  T  E  E  L  R  K  P  W  I  H  Q  L  K  N  V  I  R  Y  N
541  TAGTGACCTGGTACAGAAATACCATCCTTGCTTCTGGATTGATGGACAGTATCTCTGCTG
      S  D  L  V  Q  K  Y  H  P  C  F  W  I  D  G  Q  Y  L  C  C
601  CTCTCAGACAGCCAAGAATGCTATGGGCTGCCAAATTTTGGAGAACAGGAATGGAAGCTT
      S  Q  T  A  K  N  A  M  G  C  Q  I  L  E  N  R  N  G  S  L
661  AAAACCTGGGAGTTCTCATCGAAAAACGAAAAAGCCTCTTCCCCCTACCCCAGAGGAAGA
      K  P  G  S  S  H  R  K  T  K  K  P  L  P  P  T  P  E  E  D
721  TCAGATCTTGAAAAAACCGCTTCCCCCGGAGCCAACAGCAGCACCAATCTCCACAACCGA
      Q  I  L  K  K  P  L  P  P  E  P  T  A  A  P  I  S  T  T  E
781  GCTGAAAAAGGTCGTGGCCCTTTATGATTACATGCCAATGAACGCAAATGACTTACAATT
      L  K  K  V  V  A  L  Y  D  Y  M  P  M  N  A  N  D  L  Q  L
841  GCGAAAGGGCGAGGAGTATTTTATCCTGGAGGAGAGCAACCTACCGTGGTGGCGAGCACG
      R  K  G  E  E  Y  F  I  L  E  E  S  N  L  P  W  W  R  A  R
901  AGATAAAAATGGGCAGGAAGGCTACATCCCAAGTAACTATATCACTGAAGCTGAGGACTC
      D  K  N  G  Q  E  G  Y  I  P  S  N  Y  I  T  E  A  E  D  S
961  ATAGAGATGTATGAGTGGTATTCCAAGCACATGACTCGAAGTCAAGCTGAGCAACTGCT
      I  E  M  Y  E  W  Y  S  K  H  M  T  R  S  Q  A  E  Q  L  L
1021 AAAGCAAGAGGGGAAAGAAGGAGGTTTCATTGTCAGAGACTCCAGCAAAGCTGGAAAATA
      K  Q  E  G  K  E  G  G  F  I  V  R  D  S  S  K  A  G  K  Y
1081 CACCGTGTCTGTGTTTGCTAAATCTACTGGGGAGCCTCAAGGGGTGATCCGCCATTACGT
      T  V  S  V  F  A  K  S  T  G  E  P  Q  G  V  I  R  H  Y  V
1141 TGTGTGTTCCACGCCACAGAGCCAGTATTACCTGGCTGAGAAACACCTCTTCAGCACCAT
      V  C  S  T  P  Q  S  Q  Y  Y  L  A  E  K  H  L  F  S  T  I
```

FIG. 1A

```
1200 CCCTGAGCTCATTAACTACCATCAACACAACTCTGCAGGCCTCATATCCAGGCTGAAATA
      P  E  L  I  N  Y  H  Q  H  N  S  A  G  L  I  S  R  L  K  Y
1261 TCCTGTGTCTAAACAAAACAAAACGCGCCTTCTACTGCAGGCCTGGGCTATGGATCATG
      P  V  S  K  Q  N  K  N  A  P  S  T  A  G  L  G  Y  G  S  W
1321 GGAAATTGATCCAAAGGACCTCACCTTCTTGAAGGAGCTTGGGACTGGACAATTCGGTGT
      E  I  D  P  K  D  L  T  F  L  K  E  L  G  T  G  Q  F  G  V
1381 CGTGAAATATGGAAGTGGAGGGGCCAATATGATGTGGCCATCAAGATGATCAGAGAAGG
      V  K  Y  G  K  W  R  G  Q  Y  D  V  A  I  K  M  I  R  E  G
1441 TTCCATGTCGGAGGATGAATTCATTGAAGAAGCCAAAGTCATGATGAATCTTTCCCATGA
      S  M  S  E  D  E  F  I  E  E  A  K  V  M  M  N  L  S  H  E
1500 GAAGCTGGTGCAGTTGTATGGCGTCTGCACCAAACAACGCCCCATCTTCATCATCACCGA
      K  L  V  Q  L  Y  G  V  C  T  K  Q  R  P  I  F  I  I  T  E
1561 GTACATGGCTAATGGCTGCCTCTTGAACTACCTGAGGGAGATGCGGCACCGCTTCCAGAC
      Y  M  A  N  G  C  L  L  N  Y  L  R  E  M  R  H  R  F  Q  T
1621 ACAGCAGCTGCTTGAGATGTGCAAAGATGTCTGTGAAGCAATGGAATACTTGGAGTCGAA
      Q  Q  L  L  E  M  C  K  D  V  C  E  A  M  E  Y  L  E  S  K
1681 GCAGTTCCTTCACAGAGACCTGGCAGCTCGAAACTGTTTGGTAAACGATCAAGGAGTTGT
      Q  F  L  H  R  D  L  A  A  R  N  C  L  V  N  D  Q  G  V  V
1741 GAAAGTATCTGACTTTGGCCTGTCTAGGTATGTCCTTGATGATGAGTACACCAGCTCTGT
      K  V  S  D  F  G  L  S  R  Y  V  L  D  D  E  Y  T  S  S  V
1801 AGGCTCCAAGTTTCCAGTTCGGTGGTCTCCACCAGAAGTGCTTATGTATAGCAAGTTCAG
      G  S  K  F  P  V  R  W  S  P  P  E  V  L  M  Y  S  K  F  S
1861 CAGCAAATCTGACATCTGGGCTTTTGGGGTTTTAATGTGGGAGATCTACTCCCTGGGGAA
      S  K  S  D  I  W  A  F  G  V  L  M  W  E  I  Y  S  L  G  K
1921 GATGCCGTATGAGAGATTTACTAACAGTGAGACAGCAGAACACATTGCTCAAGGCTTACG
      M  P  Y  E  R  F  T  N  S  E  T  A  E  H  I  A  Q  G  L  R
1981 TCTCTACAGGCCTCATCTGGCATCAGAGAGGGTATATACCATCATGTACAGCTGCTGGCA
      L  Y  R  P  H  L  A  S  E  R  V  Y  T  I  M  Y  S  C  W  H
2041 CGAGAAAGCAGATGAACGTCCTAGTTTCAAAATTCTCTTGAGTAACATTCTAGATGTGAT
      E  K  A  D  E  R  P  S  F  K  I  L  L  S  N  I  L  D  V  M
2101 GGATGAAGAATCCTGAGCTGGCTCCTAACCTCCGTGGATCTCCTCCTCTCTCCTACAAAA
      D  E  E  S  *
2161 CCTAATTCCATGTTTCCTGAGGAGTTCCCTGGCTGCAGGGCTCTAGCTTCCATGCGCCTA
2221 CTGAATGCATCAAGAGCCCTGGACATCTAGGAATGCCTTTCTTCTCGTTCCCTGGCAT
2281 ACTGCTCTAAGCAAAGGTCAAGGGATTTCTGTGCCTAGTATTACCCATAACTTCAAGACT
2341 CCAACAGACTGAATTGGGGATGGGAACACTTTGGGGGAGGGAAAACTGTAAATAGCTCAC
2401 TAGTTGTCAACAGCTTGTTGTTAGTGTTAAGAGTGTGTGTGGGGGTAGGAATGTGCAT
2461 AAATGGTGTTGTAACTAATATGAAGAAAAAAAAAAAAAAAAAAAA
```

```
                                                                                          SH1
MUBPK    LLEKQEGKEGGFIVRDSSKAGKYTVSVFAKSTGEPQGVIRHYVVCSTPQS--QYYLAEKHLFSTIPELINYHQHNSAGLISRLKYPVSKQNKNAPSTAGLG    391
ITK      LLLDTGKEGAFMVRDSRTPGTYTVSVFTKAIISENPCIKHYHIKETNDSPKRYYVAEKYVVFDSIPLLIQYHQYNGGGLVTRLRYPVCSWRQKAVPTAGLR    357
TECII    LLRTEDKEGGFMVRDSSQPGLYTVSLYTKFGGEGSSGFRHYHILETATSPYY--LAEKHAFGSIPEIIEYHKHNAAGLVTRLRYPVSTKQNAPTTAGFS    333
DSRC28C  LLKQGDKEGCFVVRKSSTKGLYTLSLHTKV--PQSHVKHYHIKQNARC--EYYLSEKHCCETIPDLINYHRHNSGGLACRLKSSPC--DRPVPPTAGLS    319
HUBPK    LLKQEGKEGGFIVRDSSKAAKYTVSVFAKSTGDPGGVIRHYVVCSTPQS--QYYLAEKHLFSTIPELINYHQHNSAGLISRLKYPVSQQNKNAPSTAGLG    391

MUBPK    YGSWEIDPKDLTFLKELGTGQFGVVKYGKWRGQYDVAIKMIREGSMSEDEFIEEAKVMMNLSHEKLVQLYGVCTKQRPIFIITEYMANGCLLNYLREMRH    491
ITK      YGKWVIQPSELTFVQEIGSSGGQFGLVHLGYWLNKDKVAIKTIQEGAMSEEDFIEEAEVMMKLSHPKLVQLYGVCLEQAPICLVFEFMEHGCLSDYLRSQRG    457
TECII    YDKWEINPSELTFMRELGSGLFGVVRLGKWRAQYKVAIKAIREGAMCEEDFIEEAKVMMKLTHPKLVQLYGVCTQQKPIYIVTEFMERGCLNFLRQRQG    433
DSRC28C  HDKWEIHPIQLMLMEELGSGQFGVVRRGKWRGSIDTAVKMKEGTMSEDDFIEEAKVMTKLQHPNLVQLYGVCTKHRPIYIVTEYMKHGSLLNYLRRHEK    419
HUBPK    YGSWEIDPKDLTFLKELGTGQFGVVKYGKWRGQYDVAIKMIREGSMSEDEF                                                   442

MUBPK    RFQTQ--QLLEMCKDVCEAMEYLESKQFLHRDLAARNCLVNDQGVVKVSCFGLSRYVLDDEYTSSVGSKFPVRWSPPEVLMYSKFSSKSDIWAFGVLMWE    589
ITK      LFAAE--TLLGMCLDVCEGMAYLEKACVIHRDLAARNCLVGENQVIKVSCFGMTRFVLDDQYTSSTGTKFPVVKWASPEVFSFSRYSSKSDVWSFGVLMWE    555
TECII    HFSRR--MLLSMCQRVCEGMEYLERNSFIHRDLAARNCLVNEAGVVKVSCFGMARYVLDDQYTSSSGAKFPVKWCPPEVFNYSRFSSKSDVWSFGVLMWE    531
DSRC28C  TLIGNMGLLLDMCIQVSKGMTYLERHNYIHRDLAARNCLVGSENVAKVACFGLARYVLDDQYTSSGGTKFPIKWAPPEVLNYTRFSSKSDVWAYGVLMWE    519

MUBPK    IYSLGKMPYERFTNSETAEHIAGGLRLEYRPHLASERVYTIMYSCWHEKADERPSFKILLSNILDVMDE-ES                              659
ITK      VFSEGKIPYENRSNSEVVEDISTGFRLYKPRLASCHVYQIMNHCWKEKPEDRPPFSQLLSQLAEIAEA-GL                              625
TECII    IFTEGRMPFEKNTNYEVVTMVTRGHRLEGPKLATKYLYEVMLRCWQEESCLCRVAQDLSSK--NLIGS-RF                              583
DSRC28C  IFTCGKMPYGRLKNTEVVERVQRGIILEKPKSCAKEIYDVMKLCWSHGPEERPAFRVLMDQLALVAQTLTD                              590
```

FIG.2B

```
ACCTTCCAAG TCCTGGCATC TCAATGCATC TGGGAAGCTA CCTGCATTAA GTCAGGACTG
AGCACACAGG TGAACTCCAG AAAGAAGAAG CTATGGCCGC AGTGATTCTG GAGAGCATCT
TTCTGAAGCG ATCCCAACAG AAAAAGAAAA GATCACCTCT AAACTTCAAG AAGCGCCTGT
TTCTCTTGAC CGTGCACAAA CTCTCCTACT ATGAGTATGA CTTTGAACGT GGGAGAAGAG
GCAGTAAGAA GGGTTCAATA GATGTTGAGA AGATCACTTG TGTTGAAACA GTGGTTCCTG
AAAAAATCC TCCTCCAGAA AGACAGATTC CGAGAAGAGG TGAAGAGTCC AGTGAAATGG
AGCAAATTTC AATCATTGAA AGGTTCCCTT ATCCCTTCCA GGTTGTATAT GATGAAGGGC
CTCTCTACGT CTTCTCCCCA ACTGAAGAAC TAAGGAAGCG GTGGATTCAC CAGCTCAAAA
ACGTAATCCG GTACAACAGT GATCTGGTTC AGAAATATCA CCCTTGCTTC TGGATCGATG
GGCAGTATCT CTGCTGCTCT CAGACAGCCA AAAATGCTAT GGGCTGCCAA ATTTTGGAGA
ACAGGAATGG AAGCTTAAAA CCTGGGAGTT CTCACCGGAA GACAAAAAAG CCTCTTCCCC
CAACGCCTGA GGAGGACCAG ATCTTGAAAA AGCCACTACC GCCTGAGCCA GCAGCAGCAC
CAGTCTCCAC AAGTGAGCTG AAAAAGGAAG TGGCCCTTTA TGATTACATG CCAATGAATG
CAAATGATCT ACAGCTGCGG AAGGGTGATG AATATTTTAT CTTGGAGGAA AGCAACTTAC
CATGGTGGAG AGCACGAGAT AAAAATGGGC AGGAAGGCTA CATTCCTAGT AACGATGTCA
CTGAAGCAGA AGACTCCATA GAAATGTATG AGTGGTATTC CAAACACATG ACTCGGAGTC
AGGCTGAGCA ACTGCTAAAG CAAGAGGGGA AAGAAGGAGG TTTCATTGTC AGAGACTCCA
GCAAAGCTGC AAAATATACA CTGTCTGTGT TTGCTAAATC CACAGGGGAC CCTCAAGGG
TGATACGTCA TTATGTTGTG TGTTCCACAC CTCAGAGCCA CTACCCTG GCTGAGAAGC
ACCTTTCAG CACCATCCCT GAGCTCATTA ACTACCATCA GCACAACTCT GCAGGACTCA
TATCCAGGCT CAAATATCCA GTGTCTCAAC AAAACAAGAA TGCACCTTCC ACTGCCAGCC
TGGGATACGG ATCATGGGAA ATTGATCCAA AGGACCTGAC CTTCTTGAAG GAGCTGGGGA
CTGGACAATT TGGGGTAGTG AAGTATGGGA AATGGAGAGG CCAGTACGAC GTGGCCATCA
AGATGATCAA AGAAGGCTCC ATGTCTGAAG ATGAATTC
```

Figure 3.

HEMATOPOIETIC RESTRICTED TYROSINE KINASE (BPK)

CROSS-REFERENCE TO RELATED APPLICATIONS

This is a continuation, of application Ser. No. 08/006,449 filed Jan. 21, 1993, now abandoned, which is a continuation-in-part of application Ser. No. 07/985,998, filed on Dec. 4, 1992, now abandoned.

INTRODUCTION

1. Technical Field

The field of this invention relates to novel tyrosine kinases.

2. Background

The growth and differentiation of hematopoietic cells depends upon interaction with specific cells and molecules in the environment. The delivery of the appropriate signal can come directly from cell surface receptors which bind to specific ligands, or alternatively through association of receptors with cytoplasmic tyrosine kinases. The cytoplasmic protein tyrosine kinases can be classified into three subfamilies: the src-subfamily, the abl-subfamily and the fps-subfamily. In addition, several unclassified tyrosine kinases have been reported to be expressed in hematopoietic cells, including csk, syk, JAK1, JAK2, Tyk2 and PTK72. While some of these kinases are ubiquitously expressed (abl, src), others are more restricted and lck, hck and blk are exclusively expressed in hematopoietic cells. The general structure of cytoplasmic tyrosine kinases is characterized not only by the tyrosine-kinase catalytic domain, but also the presence of src-homology (SH) domains (reviewed in Koch, et al. (1991) *Science* 252, 668–674; Pawson and Gish, (1992) *Cell* 71, 359–362). The genes of the three subfamilies have SH2 domains, which are involved in protein-protein interactions, and in addition, src- and abl- subfamily genes have SH3 domains, which serve a regulatory function.

For most of these cytoplasmic tyrosine kinases, little is known about their essential functions. It has been reported that several of the src-subfamily tyrosine kinases are coupled to cell surface receptors in lymphocytes and function as signal transducers after specific ligand binding. Examples are the associations of CD4 and CD8 with lck, interleukin-2 receptor β chain with lck, T cell receptor complex with fyn, and the immunoglobulin receptor complex with lyn, fyn and blk. Alternatively, some cytoplasmic kinases may serve essential regulatory functions. For example, csk was reported to modify the activity of other tyrosine kinases (i.e. src-subfamily genes) and down-regulate the signal transduction pathways in which they participate.

Because of the crucial role that tyrosine kinases play in the regulation of cell growth and differentiation, the tyrosine kinases can find manifold applications. The tyrosine kinases can be used for the transduction of cells in conjunction with expression constructs to regulate the expression of genes, to identify compositions which modulate their activity or with which they naturally bind, and for use in making antibodies, as well as other purposes. In addition, where genetic defects diminish the amount of the essential tyrosine kinase, such defects may be corrected by gene therapy. Also, one may use the tyrosine kinases for specific modification of tyrosine-containing peptides, which may serve as specific substrates for individual tyrosine kinases.

SUMMARY OF THE INVENTION

A novel hematopoietic restricted tyrosine kinase is provided, both as a purified protein and a DNA sequence free of a chromosome, and fragments thereof, particularly fragments encompassing one or more functional domains. The compositions find use in identifying proteins and the DNA sequences encoding such proteins having homology to the subject compositions, for producing compositions which modulate the expression and/or function of the subject tyrosine kinase, and for studying activating pathways associated with the subject tyrosine kinases. In addition, modulation of the activity of the subject tyrosine kinases can be used for prophylactic and therapeutic purposes, in cases of gene therapy, treatment of neoplasia of cells dependent upon the functioning of the subject tyrosine kinases, treatment of non-neoplastic hyperproliferative state, e.g. associated with autoimmune diseases and allergy, identification of cell type based on the nature and amount of the subject tyrosine kinases, optionally in conjunction with other tyrosine kinases, and the like.

BRIEF DESCRIPTION OF THE FIGURES

FIG. 1 depicts the nucleotide (SEQ ID NO:1) and amino acid (SEQ ID NO:2) sequence corresponding to the nucleotide sequence of mouse and partial human BPK cDNA. The initiation codon ATG (position 137–139) is flanked by nucleotides matching with the Kozak's consensus rule. An in-frame termination codon in the 5' untranslated region as well as the poly A signal (CATAAA) in the 3' untranslated region, are dotted. SH3, SH2 and catalytic (SH1) domains of protein tyrosine kinase are indicated by dotted line, underline and box respectively.

FIG. 2 is a comparison of amino acid sequences of BPK,(SEQ ID NO:2) ITK,(SEQ ID NO:3) Dsrc28C TEC II, and (SEQ ID NO:4) (SEQ ID NO:5) (SEQ ID NO:48PK. Shaded boxes signal identity with the amino acid residues found in BPK. Gaps (–) are introduced to optimize the alignment. The beginnings of the SH3, SH2 and SH1 domains are indicated by arrows.

FIG. 3 depicts the partial nucleotide sequence of human BPK cDNA (SEQ ID NO:7).

DESCRIPTION OF THE SPECIFIC EMBODIMENTS

Methods and compositions are provided relating to a mammalian hematopoietic-restricted tyrosine kinase (BPK; B-cell Progenitor Kinase).

BPK is characterized by having an approximately 1750 to 2250 base open reading frame in a 2250 to 2750 bp cDNA, predicting a protein of about 650 to 700 amino acid residues with a calculated molecular weight of about 75 to 80 kD; the C-proximal amino acid sequence from about position 375 to the C-terminus has several motifs found in other protein tyrosine kinase (SH1) domains: (i) the ATP binding motif GTGQFG at position 409–414; the autophosphorylation site in the catalytic domain at an amino acid position of from about 545 to 555; (ii) the strong indicator sequence of tyrosine kinase specificity in subdomain VI corresponding to DLAARN (between position 500–540), the same as those of abl, fps, and csk, but different from those of src sub-family genes (DLRAAN); (iii) the consensus sequence PVRWSPPE (position 550–575), which distinguishes protein tyrosine kinases from serine-threonine kinases; (iv) amino acid sequences corresponding to SH2 (position 250–400)

and SH3 (position 210–275) domains of about 110–120 and 40–60 amino acids, respectively; (v) the absence of a hydrophobic amino acid stretch typical for transmembrane regions of receptor-type tyrosine kinases; (vi) the absence of an amino terminal myristylation signal; (vii) a short carboxyl terminus following the tyrosine kinase catalytic domain lacking the residue equivalent to tyrosine 527 of c-src; and (viii) an unusually long (greater than 200 amino acid residues) amino terminal region with a high number of basic amino acids (greater than 12 basic residues in the first 60 residues).

Mammalian BPK amino acid sequences are highly conserved, generally having greater than about 85% identity, usually greater than about 90% identity. In addition, the amino acid sequence of BPK compared with those of other tyrosine kinases by FASTA search, indicated amino acid identities of 50–60% with Dsrc28C, tac I and II. Homology is found particularly between BPK and tac II, not only in their catalytic domains but also in their unique amino terminal segments. In addition, the amino terminal segment of BPK (nucleotide numbers 137–336), has high homology (63% identity), with the 5'-untranslated sequence (nucleotide numbers 246–419) of tac I (Mano, et al. (1990) *Oncogene* 5, 1781–1786). Only 30–40% identity is found with several of the abl sub-family, the src sub-family, the fbs sub-family genes or csk.

Human BPK is characterized as being located on the midportion of the long arm of the human X-chromosome at Xq22. The gene appears to be associated with X-linked agammaglobulinemia (XLA). The human gene has about 96% amino acid identity with the mouse gene, and, therefore, has substantially the same parameters for the functional characteristics of the gene as described for the mouse gene.

Mouse BPK is characterized by having a 1977 base open reading frame in a 2505 bp cDNA (SEQ ID NO:1), predicting a protein of 659 amino acid residues with (SEQ ID NO:2) a calculated molecular weight of 76,449 D; the amino acid sequence between position 383–652 has several motifs found in other protein tyrosine kinase (SH1) domains: (i) the ATP binding motif GTGQFG at position 409–414; the autophosphorylation site in the catalytic domain at amino acid position 551; (ii) the strong indicator sequence of tyrosine kinase specificity in subdomain VI corresponding to DLAARN (position 521–526), the same as those of abl, fps, and csk, but different from those of src sub-family genes (DLRAAN); (iii) the consensus sequence PWRWSPPE (position 560–567), which distinguishes protein tyrosine kinases from serine-threonine kinases; (iv) amino acid sequences corresponding to SH2 (position 269–382) and SH3 (position 218–268) domains; (v) the absence of a hydrophobic amino acid stretch typical for transmembrane regions of receptor-type tyrosine kinases; (vi) the absence of an amino terminal myristylation signal; (vii) a short carboxyl terminus following the tyrosine kinase catalytic domain lacking the residue equivalent to tyrosine 527 of c-src; and (viii) an unusually long (217 amino acid residues) amino terminal region with a high number of basic amino acids (16 basic residues in the first 60 residues).

In addition, the amino acid sequence of BPK compared with those of other tyrosine kinases by FASTA search, indicated amino acid identities of 50–60% with Dsrc28C, tac I and II. Homology is found particularly between BPK and tec II, not only in their catalytic domains but also in their unique amino terminal segments. In addition, the amino terminal segment of BPK (nucleotide numbers 137–336), has high homology (63% identity), with the 5'-untranslated sequence (nucleotide numbers 246–419) of tec I (Mano, et al. (1990) *Oncogene* 5, 1781–1786). Only 30–40% identity is found with several of the abl sub-family, the src sub-family, the fbs sub-family genes or csk.

The expression of the subject tyrosine kinases is substantially restricted to hematopoietic cells, particularly the B-cell lineage and the myelomonocytic lineage and not the T-cell lineage. BPK transcripts are found in cells representing all stages of B-cell development, myelomonocytic cell lines and a macrophage cell line. Of 2 myeloma cell lines investigated, only one showed transcripts. BPK is a cytoplasmic tyrosine kinase as evidenced by detection of BPK in the cytosolic fraction of nuclear, membrane and cytosolic fractions obtained by differential centrifugation.

BPK is able to autophosphorylate in vitro, although demonstration of in vivo autophosphorylation was unsuccessful. BPK has transphosphorylation activity as demonstrated by the transphosphorylation of enolase, where the specificity of the transphosphorylation was demonstrated by the absence of transphosphorylation with histone H1, casein and immunoglobulin heavy chain. Furthermore, autophosphorylation of BPK in vitro becomes weak in the presence of an exogenous substrate.

The subject tyrosine kinases may be from any eukaryotic species, particularly mammalian species, such as mouse and human. These tyrosine kinases are highly conserved from species to species, so that a tyrosine kinase from any species may be isolated by means of a DNA sequence from an available tyrosine kinase, which is used as a probe for a cDNA or genomic library with low stringency. These conditions are described in the Experimental section.

The nucleic acid compositions of the subject invention may be genomic or cDNA sequences encoding all or a part of the subject BPKs. For the most part, fragments will be of at least 12 nt, more usually at least 18 nt, and preferably will include a functional domain, such as the amino terminal region, a SHx domain (where x is 1, 2 or 3 or combination thereof), and the like. The functional domains will generally be from about 60–750 nt, usually 75–700 nt. The DNA sequences may be obtained in substantial purity, and will be obtained as a sequence other than a sequence of an intact chromosome. Usually, the DNA will be obtained substantially free of other nucleic acid compounds which do not include a BPK sequence or fragment thereof, generally being at least about 50%, usually at least about 90% pure.

The DNA sequences may be used in a variety of ways. The DNA sequences may be used as probes for identifying BPK as being present in a cell, which will allow, by detection of BPK by itself or in conjunction with the detection of other tyrosine kinases, of the nature of a particular cell and its level of differentiation. They may have use in diagnosing metastatic cancers, in determining genetic diseases involving hematopoietic cells, and the like. The probes may be used for diagnosis of X-linked agammaglobulinemia, particularly in B-cells and macrophages. By the appropriate choice of a sequence which can distinguish between a wild-type and mutant B-cell kinase gene under a predetermined stringency, the presence or absence of hybrid formation will indicate the presence of the mutant gene. Thus, if the wild-type sequence is used, the absence of hybrids would indicate the mutant gene. PCR may also find use, by using the sequence as a primer. Alternatively, restriction fragment length polymorphisms may find application. Particularly, the manner in which one probes cells for the presence of particular nucleotide sequences, particularly as DNA, mRNA or cDNA, is well-established in the literature and does not require elaboration here. Conveniently, mRNA may be isolated free of DNA, and by using reverse transcriptase and PCR with primers specific for the various tyrosine kinases, the cDNAs of the tyrosine kinases may be expanded, separated on gel electrophoresis and then probed using Southern blotting or sequencing. Other techniques may also find use.

The DNA sequences, including 5' non-translated sequences, may be used as antisense sequences, in either the 5'–3' direction (the non-sense sequence) or in the 3'–5' direction. Various derivatives of the antisense sequence may be prepared, where the phosphates may be modified, where oxygens may be substituted with sulfur and nitrogen, the sugars may be modified, and the like. The antisense sequences may be used by themselves or in conjunction with various toxic moieties, such as metal chelates, sensitizers, ribozymes, and the like.

For expression, the DNA sequences may be inserted into an appropriate expression vector, where the native transcriptional initiation region may be employed or an exogenous transcriptional initiation region. A wide variety of transcriptional initiation regions are known for a wide variety of expression hosts, where the expression hosts may involve prokaryotes or eukaryotes, particularly E. coli, B. subtilis, mammalian cells, such as CHO cells, COS cells, monkey kidney cells, lymphoid cells, particularly human cell lines, and the like.

Expression cassettes may be prepared comprising the transcription initiation region, which may be constitutive or inducible, with or without an enhancer sequence, including the endogenous or heterologous enhancer sequence, the gene encoding the subject tyrosine kinase or fragment thereof, and a transcriptional termination region, optionally having a poly A sequence. The gene may be genomic, including the native introns, or cDNA gene, or portion thereof. Of particular interest, is the use of combinations of exons, which allow for the expression of particular functional domains. Also, expression cassettes may be used in gene therapy of X-linked agamma-globulinemia, where the transcriptional initiation region may be the BPK gene promoter region.

After introduction of the DNA, the cells containing the construct may be selected by means of the marker, the cells expanded and then used for expression. Where secretion is desired, a signal peptide may be joined to the sequence encoding the subject tyrosine kinases or fragments thereof, whereby the protein will be expressed, translocated through the cell membrane, and processed to remove the signal peptide.

The expression cassettes may be introduced into a variety of vectors, where the vectors will normally be characterized by the ability to provide selection of cells comprising the expression vectors. The vectors may provide for extrachromosomal maintenance, particularly as plasmids in bacteria or viruses in eukaryotic cells, or for integration, particularly in mammalian cells. Where extrachromosomal maintenance is desired, an origin sequence will be provided for the replication of the plasmid, which may be a low- or high-copy plasmid. A wide variety of markers are available for selection, particularly those which protect against toxins, more particularly against antibiotics. The particular marker which is chosen will be selected in accordance with the nature of the host, where in some cases, complementation may be employed with auxotrophic hosts, e.g. yeast. Introduction of the DNA construct may be by any convenient means, e.g. calcium-precipitated DNA, electropotation, fusion, transfection, infection with viral vectors, etc.

The subject constructs may be used in gene therapy, providing for a wild-type sequence, which may be randomly integrated or integrated by homologous recombination. By using B-cell progenitors, mature B-cells are obtained expressing the wild-type BPK. The BPK gene may be provided with its normal regulatory transcriptional initiation sequence, or a different transcriptional initiation region, where expression may be constitutive or inducible.

The subject DNA sequences may also be used for targeting for homologous recombination in embryonic stem cells, particularly mouse embryonic stem cells, to produce transgenic animals, where expression of the tyrosine kinase may be modulated, either up- or down-regulated. Thus, transgenic animals may be produced which do not express the subject tyrosine kinases or express the subject tyrosine kinases under the control of a constitutive or inducible promoter. In this way, the pathways in which the subject tyrosine kinases are involved may be elucidated, where expression of the subject tyrosine kinases may be regulated extrinsic to normal regulation.

The subject polypeptide compositions will include the entire B-cell protein kinase or useful fragments thereof, usually having at least about 10 amino acids, more usually at least about 15 amino acids and frequently not more than about 225 amino acids, particularly involving all or a major portion of a domain. Purity will be at least about 50 wt. % of the protein present preferably at least about 90 wt. %, more preferably substantially free of the proteins. The subject compositions may be modified in a variety of ways, such as conjugation with labels, e.g. radioisotopes, particles, e.g. magnetic, specific binding pair members, e.g. biotin and avidin, enzymes, fluorescers, etc., particularly labels which provide, directly or indirectly, a detectable signal. The subject compositions may be conjugated to polypeptides or proteins, either fused or through a chemical linker, to be used as immunogens for production of antibodies, to provide novel production of antibodies, to provide novel properties to the BPK, e.g. extended lifetime, attachment to a target site by means of a ligand or antibody, or the like.

The subject tyrosine kinase proteins or fragments thereof may be used in a wide variety of ways, such as kinases for phosphorylation of particular peptides, where the phosphorylation may be part of a synthetic scheme or a method of labeling a target protein, or a use as a label for identifying one or more molecules. Thus, cells could be modified to allow for expression of a gene which provides for a detectable signal in a cell. One could then screen compounds which bind to a receptor which activates the subject tyrosine kinases, where the signal-producing gene has a sequence responsive to the pathway involving the subject tyrosine kinases. In this way, various drugs can be screened to determine their activity in modulating the pathway involving the subject tyrosine kinases.

The proteins or fragments thereof may also be used for screening of compounds which bind to the subject compositions, where the compounds may serve as substrates, as inhibitors, or the like. In this manner, drugs may be screened for their utility in inhibiting the pathway, where the pathway is essential for the growth of undesired cells, e.g. B-cells involved in autoimmune diseases, or neoplastic hematopoietic cells. By combining a candidate along with a subject polypeptide composition, one may screen for complexes as indicative of binding capability and biological activity, antisera or monoclonal antibodies.

The subject compositions may also be used for producing antibodies specific for one or more domains of the subject tyrosine kinases. The antibodies may be produced in accordance with conventional ways, immunization of a mammalian host, e.g. mouse, fusion of resulting splenocytes with a fusion partner for immortalization and screening for antibodies having the desired affinity to provide monoclonal antibodies having a particular specificity. These antibodies can be used for affinity chromatography, for identifying other tyrosine kinases having similar epitopes to the subject tyrosine kinases, and the like. The antibodies may find specific use in the diagnosis of X-linked agammaglobulinemia, in accordance with conventional immunoassays. Those the antibodies may be labeled with radioisotopes, enzymes, fluorescers, chemiluminescers, or other label which will allow for detection of complex formation between the labeled antibody and its complementary epitope of BPK or other tyrosine kinase.

The subject compositions, particularly the antisense sequences, may find application in therapy, particularly involving transport of the active material into the cell. Transport can be achieved by using antibodies specific for the target cell joined to a liposome, where the active moiety is present in the lumen. Thus, the various antisense molecules described above may be introduced into the lumen and the resulting liposome/antibody conjugate compositions administered to the host, normally parenterally, more particularly, intravascularly. The compositions may be administered in any convenient physiologically-acceptable medium, such as saline, PBS, aqueous ethanol, aqueous ethylene glycols, or the like.

The particular concentration, mode of administration, frequency of administration, and the like, will be determined empirically, depending upon the particular indication, the target cells, whether the treatment is prophylactic or therapeutic, the activity of the composition, the nature of the composition and the like.

The subject compositions may also be used for phosphorylation of a variety of proteins, which may serve as substrates. This reaction may find application in assays, where the resulting substrate may be detected and the tyrosine kinase may serve as a label, e.g. ELISAs.

The following examples are offered by way of illustration and not by way of limitation.

EXPERIMENTAL

Materials and Methods
Screening and Isolation of cDNA Clone

PolyA RNA was extracted from mouse B lymphoid progenitor cells, whose characterization has been described elsewhere (Scherle et al. (1990) Proc. Natl. Acad. Sci. USA 87, 1908–1912 and Saffran et al. (1992) Curt. Top. Microbiol. Immunol. 182, 37–44), and was used to construct a cDNA library. The cDNAs were synthesized using both an oligo dT primer and random primers by the usual method (Sambrook et al. (1989) Molecular Cloning: A Laboratory Manual, Cold Spring Harbor, N.Y.). Double-stranded cDNAs were ligated to EcoRI linkers, then inserted into the EcoRI sites of λgt10, followed by in vitro packaging. This cDNA library was screened with the tyrosine kinase domain (302 bp fragment containing domains VI, VII and VIII) of the human LTK gene (Maru et al. (1990) Oncogene Res. 5, 199–204). Pre-hybridization and hybridization was carried out at 42° C. in 30% formamide, 5×SSPE, 5×Denhardt's and 0.1% SDS. The filters were washed in 2×SSC and 0.1% SDS at room temperature. After the screening and restriction analysis, cDNA inserts were subcloned into the M13 vector and sequenced by Sequenase (United States Biochemical). A cDNA library of the pre-B cell line 70z/3 was kindly provided by Michael Gilly and Randolph Wall (UCLA).

Preparation of Anti-BPK Antiserum

A DraI - HindIII fragment containing amino acids 25–173 of BPK was cloned into the bacterial expression plasmid pGEX-2T (Smith and Johnson (1988) Gene 67, 31–40). Bacterial cultures expressing this plasmid were grown in TyE containing 100 µg/ml Ampicillin and induced with 0.1 mM isopropyl-β-D-thiogalactopyranoside for 5 hr. Induced bacteria were lysed by sonication in phosphate-buffered saline (PBS), 1% Triton X-100, 50 mM EDTA, 1 mM PMSF, 100 U/ml aprotinin and 50 g/ml leupeptin, then centrifuged at 8,000 g for 5 min. Since the induced protein was insoluble, the pellet was lysed in 0.1M glycine-NaOH (pH 9.0) containing 8M urea, and fractionated by spin-column chromatography of Sephadex G-25 (Pharmacia) equilibrated in 0.1M glycine-NaOH, pH9.0 (Frorath et al. (1992) BioTechniques 12, 558–563). The passed fraction was dialysed overnight at 4° C. against PBS containing 1% Triton X-100 and purified by affinity chromatography using a gluthathione-Sepharose 4B column (Pharmacia). Eluted fusion protein was further purified using preparative SDS gel electrophoresis. Immunizations of New Zealand white rabbits were initiated by subcutaneous injections of 200 µg of purified fusion protein emulsified in complete Freund's adjuvant, followed by boosting with the same amount of protein in incomplete Freund's adjuvant every 2 weeks. Collection of sera began 4 weeks after the initial injection. Specificity and titer of the sera were examined by immunprecipitating in vitro translated BPK protein labeled with $^{35}$S-methionine.

Protein Analysis

Metabolic labeling, immunoprecipitation and in vitro kinase assays were performed as described previously (Konopka, et al. (1984), J. Virol. 31, 223–232; Konopka and Witte (1985), Mol. Cell. Biol. 5, 3116–2123). For the in vitro kinase assay, SDS was removed from the kinase lysis buffer (1% Triton X-100, 10 mM phosphate buffer pH 7.0, 150 mM NaCl), since it greatly reduced BPK-kinase activity. Optimum kinase activity was achieved in the presence of 20 mM $Mn^{2+}$ as a cofactor.

Subcellular Fractionation $5 \times 10^7$ of 70z/3 cells were labeled with 100 µCi/ml of $^{35}$S-methionine for 4 hr. The cells were suspended in hypotonic buffer (2 ml of 10 mM Tris pH 8.0, 1 mM MgCl and 0.1 mM PMSF) at 0° C. for 30 min, then were fractionated by differential centrifugation as described previously (Watanabe et al. (1984) J. Virol. 51, 620–627). Each fraction was resuspended and immunoprecipitated with anti-BPK antiserum and analyzed on a 10% SDS polyacrylamide gel.

Immunofluorescence Studies

BPK cDNA was inserted into the EcoRI site of the pSRαMSVtkneo expression vector (Muller et al. (1991) Mol. Cell. Biol. 11, 1785–1792). 15 g of plasmid DNA was transfected into COS-7 cells seeded onto coverslips by the calcium phosphate method using 15 µg of heat-denatured herring sperm DNA as a carrier. After 48 hr the coverslips were washed in ice-cold PBS three times, and subsequently fixed for a minimum of 1 hr in methanol at −20° C. Fixed cells were rehydrated in ice-cold PBS for 5 min, followed by blocking in 2.5% normal goat serum in PBS for 30 min at room temperature. This was followed by a 1 hr incubation at room temperature with a 1:100 dilution of anti-BPK antiserum in PBS. The cells were subsequently incubated for 30 min with FITC-conjugated goat anti-rabbit IgG (Oncogene Science) diluted 1:200 in PBS. After washing with PBS, fluorescent cells were detected using a Zeiss ANIOPHOT fluorescence microscope.

Northern Analysis of BPK mRNA Expression

PolyA RNA (2 µg) extracted from tissue and cell lines was electrophoresed in a denatured 1% agarose/formaldehyde gel and transferred to nitrocellulose filter. Northern filters were hybridized with $^{32}$P-labeled BPK cDNA, followed by hybridization with β-actin as control for uniform RNA loading.

Detection of the Protein Product of BPK and its Kinase Activity (A) Characterization of anti BPK antiserum BPK cDNA cloned into pBluescript was transcribed in vitro under the control of the T7 promoter. Transcribed RNA was then translated in rabbit reticulocyte lysate in the presence of $^{35}$S-methionine. The in vitro translation product was then immunoprecipitated by anti BPK antiserum. (In each experiment, the preimmune serum was used as a control.)

(B) Detection of BPK protein in vivo

70z/3 cells were metabolically labeled with 100 µCi of $^{35}$S-methionine for 4 hr and the cell lysate was immunoprecipitated by anti BPK antiserum.

(C) Kinase activity of BPK protein in vitro

BPK protein immunoprecipitated from 70z/3 cells by anti BPK antiserum was assayed for kinase activity by adding γ-$^{32}$P ATP in 20 mM PIPES (pH 7.0) containing 20 mM MnCl at 30° C., 15 min. Acid-denatured enolase was added as a substrate.

(D) Tyrosine specificity of autophosphorylation of BPK

BPK protein immunoprecipitated from 70z/3 cells by anti BPK antiserum was subjected to in vitro kinase reaction by adding cold ATP (10 µM), followed by immunoblotting with an anti-P-Tyr antibody.

(E) Anti-P-Tyr immunoblotting of BPK immunoprecipitated from 70z/3 cell lysate (without in vitro kinase reaction)

Subcellular Localization of BPK Protein (A) Subcellular fractionation

70z/3 cells were labeled with $^{35}$S-methionine for 4 hr, then suspended in hypotonic solution at 0° C. for 30 min. Cells were broken by vigorous suspension with a narrow-hole pipette. The nuclear fraction was separated by a low-speed spin (5,000 g, 10 min). Membrane and cytosolic fractions were separated by a high-speed spin (55,000 g, 25 min). Each fraction was immunoprecipitated by anti BPK antiserum and analyzed on SDS 10% polyacrylamide gel. Immunoprecipitation from crude (total) cell lysates of the same member of cells was also performed.

(B) Indirect immunofluorescence staining of COS cells expressing BP protein

COS cells were transfected with retroviral expression construct containing the BPK cDNA and stained with anti-BPK antiserum, as described in Materials and Methods. No immunofluorescence was observed with the COS cells transfected with the retrovirus containing anti-sense BPK cDNA. The light source was an HBO mercury lamp which was passed through a 450–490 nm band pass blue excitation filter. All fields were screened by an oil-immersion objective (100×magnification) and photographed onto Kodak Gold 400 film.

Unique Sequences of the Murine BPK cDNA Define a Single Gene Locus as the Human Homologue 10 ug of total human genomic DNA was digested with restriction endonucleases Hind III or EcoRI at 37° C. The digested samples were electrophoresed on a 0.8% agarose gel and transferred to nitrocellulose filters by vacuum transfer technique. Dried and baked filters were hybridized with a 2.7 kb murine BPK cDNA probe labelled by random priming technique with β$^{32}$P-ATP (Stratagene Prime-It kit, Stratagene Cloning Systems, La Jolla, Calif.). The filters were washed at high stringency (55° C. in 0.1×SSC (standard saline citrate) for 30 minutes, 3 cycles), then exposed for autoradiography. The simple single copy restriction pattern supports the contention that the murine cDNA sequence can define a single locus in the human genome which is the homologue of BPK.

Isolation of a Human BPK Cosmid Clone

A human DNA cosmid library (Denny et al., (1989) *PNAS USA* 86,4254–4258) in the cosmid vector pWE-15 (Stratagene, La Jolla, Calif.) was screened for clones which cross-hybridized with murine BPK cDNA. Plaque lifts were screened by hybridization using a BPK probe corresponding to 1.6 kb of upstream region sequence. Hybridizations were performed overnight at 42° C. in 40% deionized formamide, 4×SSc, and 10% dextran sulfate. Filters were washed two times in 0.2×SSC for 15 min at room temperature, followed by two washes at 50° C. in 2×SSC for 15 minutes. Four clones were identified and re-screened using a specific probe corresponding to 0.6 kb of the most upstream unique region of the gene. Two clones hybridizing with both probes were identified and on 28 kb clone, designated C3-1, was selected for further analysis and used as a human BPK-specific probe. A restriction map was constructed by partial restriction digestion and hybridization with T3 and T7 oligonucleotide probes flanking the clone site on either side of the insert. For Southern analysis, 10 µg of genomic DNA was restriction digested overnight at 37° C. The digested DNA was electrophoresed on an 0.8% agarose gel, transferred to nitrocellulose, and hybridized with the indicated probes.

Subclones of C3-1 were derived by digestion of cosmid DNA with Taq I and ligation of fragments to the Cla I site of the pGEM7Zf (+) vector. Colonies were screened using the upstream 0.6 kb unique region probe of murine BPK. One positive clone was identified containing BPK exonic sequence from the unique region of the gene. Plasmid DNA prepared from this clone was digested with Xba I (to remove additional intronic sequences), gel purified and religated. This sub-clone, designated U4X3, contained a 1.2 kb insert and was used as a human BPK unique region genomic probe.

Fluorescence in situ Hybridization (FISH)

The human BPK-specific cosmid probe (C3-1) was labelled by nick-translation of 500 ng of cosmid DNA in the presence of biotin-11-dUPT (Enzo Diagnostics, New York, N.Y.). In situ hybridization was performed on slides using the Oncor Light hybridization kit (Oncor, Gaithersburg, Md.) to detect single copy sequences on metaphase chromosomes. PBL of normal donors were cultured for 3 days in RPMI-1640, supplemented with 20% FCS, 3% PHA, and penicillin-streptomycin, synchronized with $10^{-7}$M methotrexate for 17 hr, and washed in unsupplemented RPMI. To enable visualization of banding after PI staining the cells were incubated with 30 µg/ml BrdU for 7 hr. The cells were arrested in metaphase after a 20 min incubation with colcemid (0.5 ug/ml) followed by hypotonic lysis in 75 mM KCl for 15 min at 37° C. Nuclear pellets were spun out and fixed in Carnoy's fixative (3:1 methanol:acetic acid). Spreads were prepared by adding a drop of the suspension onto slides and air dried.

Hybridization was performed by adding 20 ng of probe suspended in 10 µl of hybridization mix (50% formamide/2×SSC) to each slide. After sealing with a glass coverslip, the slides were incubated for 16 hr at 37° C. in a humidified chamber. Slides were washed in 50% formamide/2×SSC for 20 min at 43° C., and 2×SSC for 10 min at 37° C. Hybridized probe was detected by incubation of the slides with FITC-avidin according to the manufacturer's protocol (Oncor). Chromosomes were counterstained with PI suspended in mounting medium to facilitate identification, which was confirmed by sequential TG-banding (Cannizarro and Emanuel, *Cytogenet. Cell Genet.* (1984) 38, 308–309). Slides were visualized using a Leitz Orthoplan 2 epifluorescence microscope and photographed with Kodak Gold ASA 400 film.

Somatic Cell Hybrid Analysis

Somatic cell hybrids were isolated from the fusion of mouse A9 cells or Chinese hamster 1102 cells (each deficient in HPRT) with normal human cells or human cells with X-chromosome/autosome translocations (obtained from the Mutant Cell Repository, Camden, N.J.) using methods previously described (Mohandas, et al., *Somat. Cell. Mol. Genet.* (1986) 12, 89–94). Clones 99-4X and 74.7 contained a structurally normal human X-chromosome only in the A9 and 1102 background, respectively. The following clones retained only truncated human X-chromosomes: 31-1 (A9 x GM7792, t(X;20) (q11;q11)); 11-4 (1102 x GM1409, t(X;9) (q13;q34)); 50-2B (A9 x GM1696, t(X;7) (q21;p22)); 32-23 (A9 x GM2621, t(X;12) (q22;q24)); 100-1 (A9 x GM0089, t(X;19) (q22;q13.3)); 33–16 (A9 x GM0097A, t(X;1) (q26;q12)). The GM numbers refer to the Mutant Cell Repository directory.

DNA from each hybrid (10 μg) was digested with Hind III overnight at 37° C., separated by agarose gel electrophoresis (0.8% agarose gel), transferred to NC by vacuum blotting, UV crosslinked and prehybridized as described at 42° C. (Sambrook, et al., *Molecular Cloning. A Laboratory Manual* (1989), CSHL, CSHL Press). Filters were hybridized with the U4X3 subclone of the human BPK cosmid C3-1, after random primer labeling (Stratagene, Prime-It) at 42° C. overnight. Filters were washed at 55° C. in 0.2× SSC for 45 min and autoradiography performed.

DNA from 4 patients with the X-linked eye disorder, choroideremia, was obtained as a gift from Dr. R. Nussbaum (U. Penn., Dept. of Genetics). DNA from each patient (10 g) was digested with Hind III and used for Southern blot analysis as described above.

Southern Blot, Pulse Field Gel Electrophoresis, and YAC Analysis

The preparation of high molecular weight DNA, digestion with restriction enzymes, electrophoresis and Southern blotting was performed using standard techniques (Sambrook, et al., 1989, supra.). Construction of YACs (Allen and Belmont, *Human Mol. Genet.* (1992) 1, 216) and pulse field gel electrophoresis (PFGE) of genomic DNA and YACs was performed in accordance with conventional techniques. Probes used for Southern analysis were prepared as described above.

Cell Lines and Patient Samples

The normal cell lines III-6 and III-7, carrier cell lines ELB-5, ELB-10 and EKG-4.59, and XLA cell lines BT-8, BDB-BM and BDB-30 were derived by transformation with the EBV-producing B95.8 marmoset cell line as previously described (Kubagawa, et al., *PNAS USA* (1988) 85,875–879). The XLA cell lines D.C. and C.C. were derived by transformation with supernatants from the EBV-producing line MCUV as described (Conley, et al., *NEJM* (1986) 315, 564–567).

Protein Analysis

Metabolic labeling, immunoprecipitation and in vitro kinase assays were performed as described previously (Konopka, et al., *J. Virol.* (1984) 51, 223–232; Konopka and Witte, *Mol. Cell. Biol.* (1985) 5, 3116–3123). For the in vitro kinase assay, SDS was removed from the kinase lysis buffer (1% Triton X-100, 10 mM phosphate buffer pH 7.0, 150 mM NaCl), since it greatly reduced BPK-kinase activity. Optimum kinase activity was achieved in the presence of 20 mM $Mn^{2+}$ as a cofactor.

RNA Analysis

RNA was extracted from cells by standard procedures described previously (McLaughlin, et al., 1987). For northern analysis, 20 μg of total RNA was electrophoresed on formaldehyde/agarose gels, transferred to nitro-cellulose, and probed with a 2.0 kb human BPK partial cDNA containing the unique region of BPK, then stripped and reprobed with β-actin cDNA to assess RNA loading. Exposure time was 24 h.

Isolation of a Human BPK cDNA Clone

A human cDNA library derived from the human erythroleukemia cell line K562 (Mes-Masson, et al., *PNAS USA* (1986) 83, 9768–9772) was screened for human BPK cDNA clones. A murine BPK probe corresponding to 1.6 kb of upstream region was hybridized to filter lifts from approximately $5 \times 10^5$ plaques generated from size-selected RNA (>2 kb). Hybridization conditions were 50% formamide/ 4× SSC at 42° C. overnight. Filters were washed two times in 2× SSC for 15 min at room temperature, followed by two more washes in 0.2× SSC for 15 min at 50° C. Four positive clones were identified, which were screened again using the most upstream unique region murine BPK cDNA probe (0.6 kb). One of four clones was positive, called K1-1, containing 2 kb of sequence including translated sequences and the most 5' untranslated region. Nucleic acid and protein sequences for the murine and human BPK cDNA clones are deposited in GenBank.

RESULTS

BPK Belongs to a Novel Subfamily of Cytoplasmic Tyrosine Kinases

A cDNA library prepared from B lymphoid progenitors was screened with the tyrosine kinase domain sequence of the human LTK gene under reduced stringency. One clone contained a homologous but unique sequence in comparison to the catalytic domains of several known tyrosine kinases. A cDNA library of the 70z/3 pre-B cell line using this clone as the probe was screened and a full-length cDNA was obtained. FIG. 1 shows the total nucleotide and predicted amino acid sequence of this gene. This gene is designated as BPK (B-cell Progenitor Kinase). The nucleotide sequence (SEQ ID NO:1) of this clone was 2505 base pairs in length and contained a 1977 base open reading frame which predicted a protein of 659 amino acid residues (SEQ ID NO:2) with a calculated molecular weight of 76,449 daltons. The amino acid sequence between position 383–652 of BPK had several motifs found in other protein tyrosine kinase (SH1) domains (Hanks et al. (1988) *Science* 241, 42–52). The putative ATP binding motif, GTGQFG, was found at position 409–414, and the putative autophosphorylation site in the catalytic domain was conserved at amino acid position 551. The strong indicator sequence of tyrosine kinase specificity in subdomain VI corresponded to DLAARN (position 521–526) in BPK, which was the same as those of abl, fps, csk, but different from those of src-subfamily genes (DLRAAN). BPK contained another consensus sequence, PVRWSPPE (position 560–567), which distinguishes protein tyrosine kinases from serine-threonine kinases. Amino acid sequences corresponding to SH2 (269–382) and SH3 (218–268) domains were also present. BPK lacked the hydrophobic amino acid stretch typical for transmembrane regions of receptor type tyrosine kinases.

Sequence comparisons at the amino and carboxyl terminal regions of BPK had several distinguishing features from members of known tyrosine kinase subfamilies. First, an amino terminal myristylation signal (a glycine at residue 2 and lysine (or arginine) at position 7), essential for post-translational myristylation (Kaplan et al. (1988) *Mol. Cell. Biol.* 8, 2435–2441), is not found in the sequence of BPK. The first methionine was followed by alanine, and the seventh residue was glutamic acid. Second, the short carboxyl terminus following the tyrosine kinase catalytic domain of BPK lacked the residue equivalent to the tyrosine 527 of c-src. This tyrosine is conserved in all members of the src-family genes (Kmiecik and Shalloway (1987) *Cell* 49, 65–73 and Piwnica-Worms et al. (1987) *Cell* 49, 75–82). Lastly, the amino terminal region of BPK, known as the unique region of cytoplasmic tyrosine kinases, was unusually long (217 amino acid residues), when compared with those of the src-subfamily (70–100 amino acid residues). In this region BPK contained a high number of basic amino acids (16 basic residues in the first 60 residues).

Figure 2A:
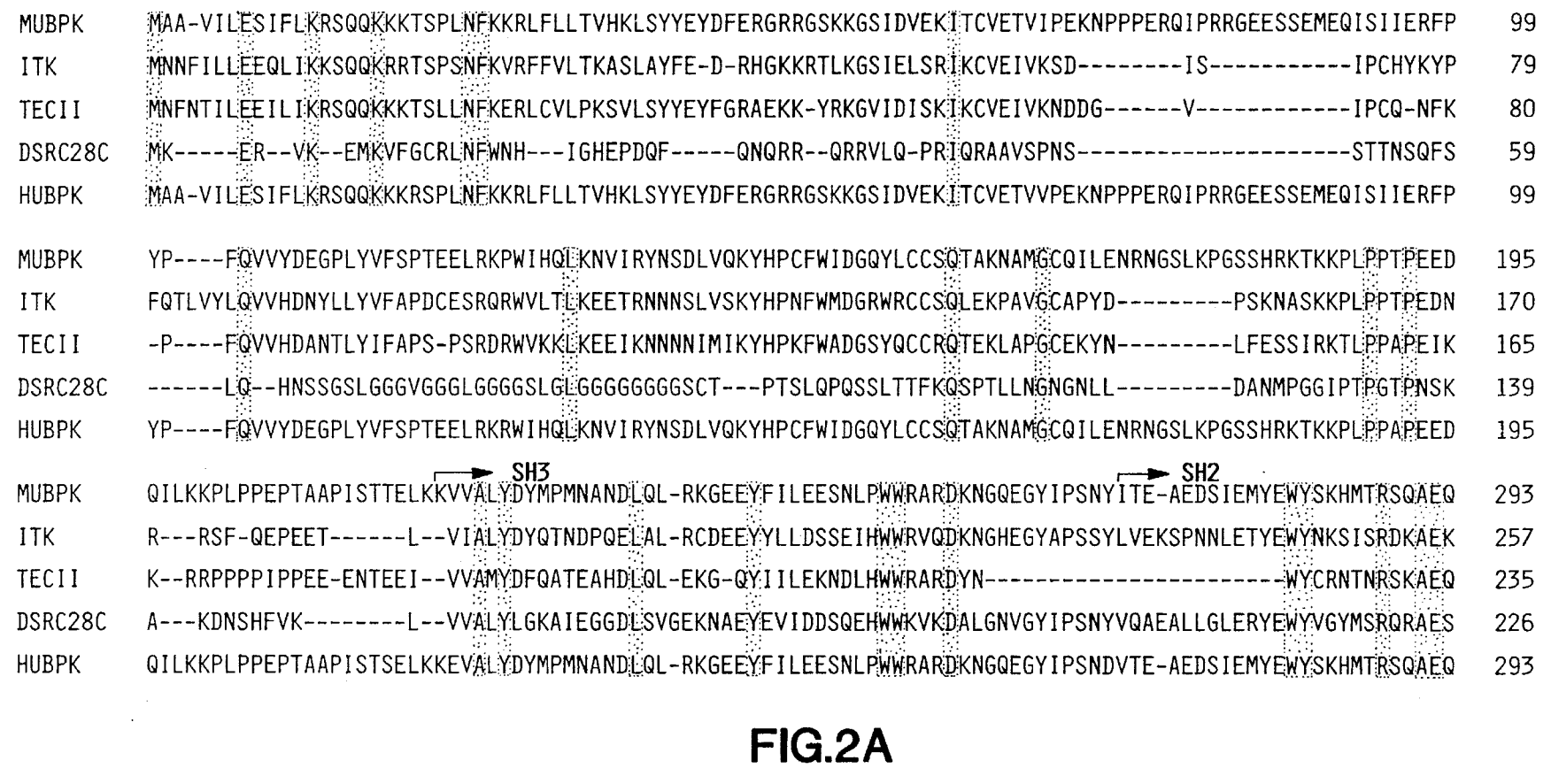

The deduced amino acid sequence of BPK was compared with those of other tyrosine kinases by FASTA search (Lipman and Pearson (1985) *Science* 227, 1435–1441). Amino acid identities of 50–60% were observed for Dsrc2BC, tacI and tacII cytoplasmic tyrosine kinases (FIG. 2). Especially high homology was found between BPK and tacII, not only in their catalytic domains but also in their unique amino terminal segment. In addition, the amino terminal segment of BPK (nucleotide no. 137–336) had high homology (63% identity) with the 5'-untranslated sequence (nucleotide no. 246–419) of tacI (Mano et al. (1990) *Oncogene* 5, 1781–1786) on the nucleotide level. This homology may suggest the possibility of alternative splicing between tecI and tecII, or a sequence error in the 5'-untranslated region of tacI. In contrast, only 30–40% identity was found with several of the abl-subfamily, the src-subfamily, the fps-subfamily genes or csk. In addition to the high identity, several features of the deduced amino acid sequence of BPK were shared with Dsrc28C, tacI and tacII. These included: 1) lack of myristylation signals, 2) lack of carboxyl terminal regulatory phosphorylation sites, 3) long, basic amino terminal regions (In the case of tacI, the amino terminal region is not basic, although the nucleotide sequence of 5'-untranslated region of tacI has high homology with the basic amino terminal segment of BPK, as described above.), and 4) presence of SH2 and SH3 domains. These common features among BPK, Darc28C, tecI and tecII suggests that these genes create a new subfamily of cytoplasmic tyrosine kinases. Interestingly the computer search also showed a moderate homology (21 amino acid identity in 106 residues) between the unique amino terminal segment of BPK (position 19–124) and the extracellular domain of the cation-independent mannose 6-phosphate receptor (position 1008–1116). homologous region exists in domains 7 and 8 of the cation-independent mannose 6-phosphate receptor gene (Lobel et al. (1988) *J. Biol. Chem.* 263, 2563–2570). The significance of this homology is unknown.

Cell Lineage Specific Expression of BPK Transcripts

To determine the expression pattern of BPK transcripts, polyA RNA was extracted from various murine tissues and analyzed by Northern hybridization using BPK cDNA as the probe.

TABLE 1

Expression of BPK.

| Tissue | | Cell lines | | Cell lines | |
|---|---|---|---|---|---|
| brain | − | B-lineage | | Myelomonocytic | |
| spleen | +++ | pro-B | | DAGM | +++ |
| thymus | + | HAFTL-1 | +++ | WEHI3 | +++ |
| kidney | − | pre-B | | 32D | +++ |
| liver | − | 38B9 | +++ | HL-60 | +++ |
| bone marrow | +++ | CL18-8 | +++ | PLB985 | +++ |
| muscle | − | 18.81 | +++ | U937 | +++ |
| heart | − | 70z/3 | +++ | Macrophage | |
| lymph node | +++ | B | | P388D1 | +++ |
| lung | + | WEHI231 | +++ | Erythrocyte | |
| testis | − | Myeloma | | HEL | +++ |
| ovary | − | S107 | +++ | K562 | +++ |
| salivary gland | − | P3X | − | | |
| fetal liver* | +++ | | | Fibroblast | |
| yolk sac* | − | T-lineage | | NIH3T3 | − |
| | | DN7.1 | − | S17 | − |
| | | KKT-2 | − | | |
| | | EL-4 | − | | |
| | | Jurkat | − | | |

Semiquantitated as follows: +++ high; ++ moderate; + weak; − undetectable.
*From 14-day fetus.

A major 3 kb transcript was detected in bone marrow, spleen, lymph node and faintly in thymus of adult mice and murine fetal liver (day 14), but not in non-hematopoietic tissues. Expression of BPK transcripts was further examined in various hematopoietic cell lines (Table 1). BPK transcripts were detected in cell lines representing all stages of B cell development, myelomonocytic cell lines and a macrophage cell line. The only B cell line tested that did not express the BPK transcript was P3X, a myeloma cell line, although another myeloma cell line, S107, expressed the BPK transcript. Transcripts of BPK were not detected in T-lineage cell lines.

Detection of BPK Protein and Its Tyrosine Kinase Activity

The expression of BPK gene products was investigated using an antiserum prepared against the amino terminal unique region (see Materials and Methods). The specificity of this antiserum was demonstrated by immunoprecipitating in vitro translated BPK protein labeled with S-methionine.

In vitro translated BPK proteins exhibited molecular weights of 77 (corresponding to the full length amino acid sequence), 66, 58 and 50 kd (corresponding to translational initiations at internal methionines). Antiserum against the amino terminal region of BPK efficiently precipitated the 77 and 66 kd translation products. This antiserum has used for the detection of BPK protein in vivo. Several cell lines were metabolically labeled with $^{35}$S-methionine and immunoprecipitated with anti-BPK antiserum. The major protein species of 77 kd was detected in B-lineage cells and myelomoncytic cells. The appearance of the 77 kd protein correlated with the expression pattern of BPK transcripts among B-lineage cells tested.

The kinase activity of BPK was examined by an in vitro kinase assay. Cell lysates of 70z/3 were immunoprecipitated by anti-BPK antiserum and assayed for autokinase activity. The results demonstrated that BPK protein is able to catalyze the autophosphorylation reaction. Furthermore, BPK had transphosphorylation activity for enolase; histone H1, casein and immunoglobulin heavy chain were not phosphorylated. In the presence of the exogenous substrate, autophosphorylation of BPK became weak, which may reflect the effect of substrate-competition or preference for transphosphorylation by the BPK kinase activity. BPK protein immunoprecipitated from 70z/3 cell lysate was immunoblotted with anti-P-Tyr antibody after an in vitro kinase reaction. The appearance of the 77 kd band showed that BPK protein was autophosphorylated on tyrosine residues in vitro. Phosphoamino acid analysis of in vitro labeled BPK protein revealed that only tyrosine residues were autophosphorylated. However, tyrosine phosphorylation of BPK in vivo was not diluted by anti-P-Tyr blotting of BPK protein precipitated from 70z/3 cell lysate. This may correspond to the absence of the carboxyl terminal regulatory phosphorylation site in BPK.

BPK Protein Localizes in the Cytoplasm

To determine the subcellular localization of the BPK protein, differential centrifugation was performed of $^{35}$S-methionine labeled 70z/3 cells to obtain nuclear, membrane, and cytosolic fractions. Each fraction was then subjected to immunoprecipitation with anti-BPK antiserum. The results showed that almost all of the BPK protein was present in the cytosolic fraction. To further confirm the cytosolic localization of BPK, COS cells were transfected with a retroviral expression construct containing the BPK cDNA. Indirect immunofluorescence staining showed that the cytoplasm was stained at a high level. No nuclear or accentuated cell membrane staining was detected.

BPK Maps to the Long Arm of the X-chromosome (Xq22) by Fluorescence in vitro Hybridization and Somatic Cell Hybrid Analysis Cosmid, C3-1, was selected on the basis of hybridization to a murine unique region probe after secondary screening. A more restricted unique region subclone (U4X3) a 5 kbp sequence proximal to the 3'terminus was derived from C3-1. The U4X3 unique region and murine BPK cDNA probes revealed restriction fragments of identical size in Southern blot analysis of human genomic DNA. The location of the U4X3 subclone was established by hybridization to specific, restriction fragments mapped within the cosmid clone C3-1. Both the full length cosmid clone (C3-1) and the unique region subclone U4X3 were used as human-specific BPK probes.

Fluorescence in vitro hybridization (FISH) was used to determine the chromosomal localization of human BPK. The 28 kb BPK-specific cosmid clone C3-1 was hybridized to metaphase spreads. Fluorescent microscopy revealed twin fluorescent dots on sister chromatids of the X-chromosome in female metaphase spreads. This was confirmed by simultaneous hybridization with an alpha satellite probe, specific for repeat sequences on the X-centromere, and the C3-1 probe. A photomicrograph demonstrated that BPK-specific twin dots were present on both X-chromosomes, positively identified by the intensely staining satellite probe. When staining male chromosome spreads, fluorescent twin dots were only present on the single X-chromosome.

To determine the specific region of hybridization on X, ratios of centromere to probe:centromere to telomere distances were calculated from photomicrographs and plotted against an X-chromosome band map archetype (Harden and Klinger, eds., An international system for human cytogenetics, (Basil; Karger) 1985). From 10 independent metaphase spreads 6 fluorescent signals were localized to Xq22, 2 to Xq21.3, and 2 to Xq23.

To independently confirm the X-localization of BPK, a panel of rodent-human somatic cell hybrids containing normal or reduced human X-chromosomes were evaluated. The BPK human cosmid subclone, U4X3, containing exonic sequence from the unique region of the gene was used for hybridization with somatic cell hybrid DNA in Southern blot analysis. The BPK probe hybridized specifically with DNA from somatic hybrids containing the entire human X-chromosome and to DNA from reduced X-chromosome cell lines containing regions overlapping Xq21-22. There was no hybridization with X-chromosomal regions telomeric to Xq22. These results were further confirmed by Southern blot analysis using DNA specimens from individuals containing X-chromosomal deletions resulting in the eye disorder, choroideremia. The U4X3 probe hybridized with DNA specimens with large X-chromosome deletions spanning Xq21.1-Xq21.3. These results and those obtained by FISH independently localized the human BPK gene to Xq22.

The BPK Gene is Tightly Linked to the Region of Xq22 Identified as the XLA Region Locus The gene for XLA has been mapped to the midportion of the long arm of the X-chromosome at Xq22. In linkage studies of more than 500 individuals in over 60 informative families, no recombination has been detected between XLA and a probe (p212) with an LOD score greater than 11 recognizing a polymorphism at DXS178 (Kwan, et al., Genomics (1990) 6,238–242). The closest reported flanking markers, at DXS442 and DX94, are approximately 3 cM apart. To localize the gene for BPK more precisely, the U4X3 human cosmid unique sequence probe was used to screen a panel of yeast artificial chromosome (YAC) clones that formed a partial contig map in the region defined by the flanking markers. The BPK probe hybridized with a 200 kb YAC, designated A2. This YAC had been previously isolated using the probe most closely linked to XLA, p212. The A2 YAC also hybridized to murine BPK cDNA probes. All 5 YAC clones isolated with a probe, A2R, defining one of the ends of the human insert in the A2 YAC, were also positive with the BPK cosmid probe. None of 21 additional YACs, including a YAC containing human sequence from the opposite end of the A2 YAC, were recognized by the BPK cosmid probe. Further restriction mapping demonstrated that the BPK gene was within 60 kb of the end of the A2 YAC, and within 100 kb of the XLA linked p212 probe. These results demonstrate that the BPK gene is very tightly linked to the region of Xq22 identified as the XLA region locus.

In an attempt to identify deletions in the BPK gene, genomic DNAs from multiple patients with XLA were evaluated by Southern analysis. Using a panel of multiple restriction enzymes and several probes, including the human BPK cosmid unique region and full length or subfragment murine and human cDNA sequences, no unique RFLPs were identified. This supports the conclusion that a common, large deletion in the coding region of BPK was unlikely. Small deletions, point mutations or alterations in distant upstream exons of BPK, not covered by the available probes, however, remained possible.

Deficient Expression of BPK in EBV-Transformed B-Cell Lines From XLA Patients

To directly address whether BPK expression was altered in XLA, B-cell lines derived from affected individuals were evaluated. A panel of EBV-transformed pre-B and B-cell lines from normals, obligate carriers, and patients with XLA was examined for potential alteration in expression or function of BPK. Lines were derived from unaffected individuals, obligate carriers of XLA, and XLA affected patients. In both groups, the lines represented early (sIgM −) and late (sIgM +) stages of B-cell development derived from both bone marrow and peripheral blood lymphocytes. Lines represented patients with both typical and milder disease phenotypes.

Using the polyclonal antiserum recognizing human BPK, lysates from normal and XLA lines were immunoprecipitated and tested for kinase activity in an in vitro autokinase assay. Strikingly, BPK kinase activity was undetectable or deficient in all XLA patient derived cell lines. Lines from normals and obligate carriers expressed kinase activity similar to the control B-cell line RAJI. Notably, one XLA B-cell line produced a diminished but detectable level of kinase activity. This line was derived from an individual with late onset of recurrent bacterial infection and possibly a milder disease phenotype.

The decrease in kinase activity of BPK in the XLA lines did not appear to be due to the presence of a nonspecific trans-acting phosphatase or inhibitor. The autokinase activity of an unrelated kinase, c-abl, was evaluated using protein extracted from each of the cell lines. All lines demonstrated equivalent levels of c-abl autokinase activity.

Explanations for the absence of kinase activity in XLA cell lines would include mutations in the kinase domain or deficient production of BPK protein. To examine the latter possibility, lysates from $^{35}$S-methionine labelled control and XLA cell lines were used for immunoprecipitation with polyclonal Ab recognizing the BPK unique region. All tested XLA lines had absent or decreased protein expression which paralleled the level of autokinase activity. This result argued against a mutation in the kinase domain, but led to the possibility of deficient BPK mRNA expression in the XLA cell lines.

To evaluate BPK mRNA expression, total RNA prepared from EBV cell lines was analyzed by northern blotting using human BPK cDNA as a probe (see Experimental Procedures). Normal B-cell lines expressed the 3.0 kb BPK transcript, while XLA lines expressed little to no detectable level of the BPK transcript. The reduction or absence of mRNA transcripts in patient cell lines explains the lack of immuno-reactive protein and kinase activity. Low but detectable amounts of BPK mRNA were present in two affected individuals upon extended exposure of the autoradiographs. In one XLA line, D.C., this expression was consistent with the low levels of detectable protein and kinase activity observed. Interestingly, in the XLA cell line, BT-8, there was detectable mRNA expression, yet no detectable kinase activity. It is likely that these XLA lines represent distinct mutations producing transcripts with differing effects on mRNA stability, protein expression or function.

It is evident from the above results that novel compositions are provided having tyrosine phosphorylation capability, as well as methods of preparing these compositions and using these compositions. Because of the restricted nature of the subject tyrosine kinase, being restricted to hematopoietic cells, the subject tyrosine kinase compositions may find a wide variety of uses in elucidating the various compositions involved with the subject tyrosine kinase activation pathway, modulation of the tyrosine kinase activity both for prophylactic and therapeutic purposes, in assays, both for the subject compositions and for other compositions in conventional immunoassays and the like.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A purified cDNA which encodes a polypeptide selected from the group consisting of SEQ ID NO:2 and SEQ ID NO:6.

2. A purified DNA according to claim 1, wherein said DNA consists of the sequence of SEQ ID NO:1, or the complement thereof.

3. A purified DNA according to claim 1, wherein said DNA consists of the sequence of SEQ ID NO:7, or the complement thereof.

4. A cell comprising a DNA according to claim 1.

5. A cell according to claim 4, wherein a transcriptional initiation region is 5' to said DNA sequence and said DNA sequence is under the transcriptional regulatory control of said transcriptional initiation region.

6. A purified cDNA, wherein the nucleotide sequence of said cDNA or the complement thereof is selected from the group consisting of SEQ ID NO:1 and SEQ ID NO:7.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 2505 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 137..2116

( x i ) SEQUENCE DESCRIPTION: SEQ ID NO:1:

```
TAAGAATATG TCTCCAGGTC CAGAGTCTTC AGAGATCAAG TCCCACCTTC CAAGTCCTGG                                     60

CATCTCACGA CGTCTGGGGA GCTACCTGCA TTAAGTCAGA ACTGAGTACA CAAACAAGTT                                    120

CCAGAGAGAG GAAGCC ATG GCT GCA GTG ATA CTG GAG AGC ATC TTT CTG                                       169
              Met Ala Ala Val Ile Leu Glu Ser Ile Phe Leu
               1              5                    10

AAG CGC TCC CAG CAG AAA AAG AAA ACA TCA CCT TTA AAC TTC AAG AAG                                     217
Lys Arg Ser Gln Gln Lys Lys Lys Thr Ser Pro Leu Asn Phe Lys Lys
            15              20                  25

CGC CTG TTT CTC TTG ACT GTA CAC AAA CTT TCA TAC TAT GAA TAT GAC                                     265
Arg Leu Phe Leu Leu Thr Val His Lys Leu Ser Tyr Tyr Glu Tyr Asp
        30              35                  40

TTT GAA CGT GGG AGA AGA GGC AGT AAG AAA GGT TCA ATA GAT GTT GAG                                     313
Phe Glu Arg Gly Arg Arg Gly Ser Lys Lys Gly Ser Ile Asp Val Glu
        45              50                  55

AAG ATC ACC TGT GTT GAA ACA GTA ATT CCT GAA AAA AAT CCC CCA CCA                                     361
Lys Ile Thr Cys Val Glu Thr Val Ile Pro Glu Lys Asn Pro Pro Pro
60              65                  70                  75

GAA AGA CAG ATT CCG AGG AGA GGT GAG GAG TCT AGT GAA ATG GAA CAG                                     409
Glu Arg Gln Ile Pro Arg Arg Gly Glu Glu Ser Ser Glu Met Glu Gln
            80                  85                  90

ATT TCA ATC ATT GAA AGG TTC CCG TAC CCA TTC CAG GTT GTA TAT GAT                                     457
Ile Ser Ile Ile Glu Arg Phe Pro Tyr Pro Phe Gln Val Val Tyr Asp
            95                  100                 105

GAA GGA CCT CTC TAT GTT TTC TCC CCA ACT GAA GAG CTG AGA AAG CGC                                     505
Glu Gly Pro Leu Tyr Val Phe Ser Pro Thr Glu Glu Leu Arg Lys Arg
        110             115                 120

TGG ATT CAC CAG CTC AAA AAT GTA ATC CGG TAC AAT AGT GAC CTG GTA                                     553
Trp Ile His Gln Leu Lys Asn Val Ile Arg Tyr Asn Ser Asp Leu Val
    125             130                 135

CAG AAA TAC CAT CCT TGC TTC TGG ATT GAT GGA CAG TAT CTC TGC TGC                                     601
Gln Lys Tyr His Pro Cys Phe Trp Ile Asp Gly Gln Tyr Leu Cys Cys
140             145                 150                 155

TCT CAG ACA GCC AAG AAT GCT ATG GGC TGC CAA ATT TTG GAG AAC AGG                                     649
Ser Gln Thr Ala Lys Asn Ala Met Gly Cys Gln Ile Leu Glu Asn Arg
            160                 165                 170

AAT GGA AGC TTA AAA CCT GGG AGT TCT CAT CGA AAA ACG AAA AAG CCT                                     697
Asn Gly Ser Leu Lys Pro Gly Ser Ser His Arg Lys Thr Lys Lys Pro
        175                 180                 185

CTT CCC CCT ACC CCA GAG GAA GAT CAG ATC TTG AAA AAA CCG CTT CCC                                     745
Leu Pro Pro Thr Pro Glu Glu Asp Gln Ile Leu Lys Lys Pro Leu Pro
        190                 195                 200

CCG GAG CCA ACA GCA GCA CCA ATC TCC ACA ACC GAG CTG AAA AAG GTC                                     793
Pro Glu Pro Thr Ala Ala Pro Ile Ser Thr Thr Glu Leu Lys Lys Val
    205                 210                 215

GTG GCC CTT TAT GAT TAC ATG CCA ATG AAC GCA AAT GAC TTA CAA TTG                                     841
Val Ala Leu Tyr Asp Tyr Met Pro Met Asn Ala Asn Asp Leu Gln Leu
220             225                 230                 235

CGA AAG GGC GAG GAG TAT TTT ATC CTG GAG GAG AGC AAC CTA CCG TGG                                     889
Arg Lys Gly Glu Glu Tyr Phe Ile Leu Glu Glu Ser Asn Leu Pro Trp
            240                 245                 250

TGG CGA GCA CGA GAT AAA AAT GGG CAG GAA GGC TAC ATC CCA AGT AAC                                     937
Trp Arg Ala Arg Asp Lys Asn Gly Gln Glu Gly Tyr Ile Pro Ser Asn
            255                 260                 265

TAT ATC ACT GAA GCT GAG GAC TCC ATA GAG ATG TAT GAG TGG TAT TCC                                     985
Tyr Ile Thr Glu Ala Glu Asp Ser Ile Glu Met Tyr Glu Trp Tyr Ser
            270                 275                 280

AAG CAC ATG ACT CGA AGT CAA GCT GAG CAA CTG CTA AAG CAA GAG GGG                                    1033
Lys His Met Thr Arg Ser Gln Ala Glu Gln Leu Leu Lys Gln Glu Gly
        285                 290                 295
```

| | | | | | | | | | | | | | | | | |
|---|---|---|---|---|---|---|---|---|---|---|---|---|---|---|---|---|
| AAA | GAA | GGA | GGT | TTC | ATT | GTC | AGA | GAC | TCC | AGC | AAA | GCT | GGA | AAA | TAC | 1081 |
| Lys 300 | Glu | Gly | Gly | Phe | Ile 305 | Val | Arg | Asp | Ser | Ser 310 | Lys | Ala | Gly | Lys | Tyr 315 | |
| ACC | GTG | TCT | GTG | TTT | GCT | AAA | TCT | ACT | GGG | GAG | CCT | CAA | GGG | GTG | ATC | 1129 |
| Thr | Val | Ser | Val | Phe 320 | Ala | Lys | Ser | Thr | Gly 325 | Glu | Pro | Gln | Gly | Val 330 | Ile | |
| CGC | CAT | TAC | GTT | GTG | TGT | TCC | ACG | CCA | CAG | AGC | CAG | TAT | TAC | CTG | GCT | 1177 |
| Arg | His | Tyr | Val 335 | Val | Cys | Ser | Thr | Pro 340 | Gln | Ser | Gln | Tyr | Tyr 345 | Leu | Ala | |
| GAG | AAA | CAC | CTC | TTC | AGC | ACC | ATC | CCT | GAG | CTC | ATT | AAC | TAC | CAT | CAA | 1225 |
| Glu | Lys | His 350 | Leu | Phe | Ser | Thr | Ile 355 | Pro | Glu | Leu | Ile | Asn 360 | Tyr | His | Gln | |
| CAC | AAC | TCT | GCA | GGC | CTC | ATA | TCC | AGG | CTG | AAA | TAT | CCT | GTG | TCT | AAA | 1273 |
| His | Asn 365 | Ser | Ala | Gly | Leu | Ile 370 | Ser | Arg | Leu | Lys | Tyr 375 | Pro | Val | Ser | Lys | |
| CAA | AAC | AAA | AAC | GCG | CCT | TCT | ACT | GCA | GGC | CTG | GGC | TAT | GGA | TCA | TGG | 1321 |
| Gln 380 | Asn | Lys | Asn | Ala | Pro 385 | Ser | Thr | Ala | Gly | Leu 390 | Gly | Tyr | Gly | Ser | Trp 395 | |
| GAA | ATT | GAT | CCA | AAG | GAC | CTC | ACC | TTC | TTG | AAG | GAG | CTT | GGG | ACT | GGA | 1369 |
| Glu | Ile | Asp | Pro | Lys 400 | Asp | Leu | Thr | Phe | Leu 405 | Lys | Glu | Leu | Gly | Thr 410 | Gly | |
| CAA | TTC | GGT | GTC | GTG | AAA | TAT | GGG | AAG | TGG | AGG | GGC | CAA | TAT | GAT | GTG | 1417 |
| Gln | Phe | Gly | Val 415 | Val | Lys | Tyr | Gly | Lys 420 | Trp | Arg | Gly | Gln | Tyr 425 | Asp | Val | |
| GCC | ATC | AAG | ATG | ATC | AGA | GAA | GGT | TCC | ATG | TCG | GAG | GAT | GAA | TTC | ATT | 1465 |
| Ala | Ile | Lys | Met 430 | Ile | Arg | Glu | Gly | Ser 435 | Met | Ser | Glu | Asp | Glu 440 | Phe | Ile | |
| GAA | GAA | GCC | AAA | GTC | ATG | ATG | AAT | CTT | TCC | CAT | GAG | AAG | CTG | GTG | CAG | 1513 |
| Glu | Glu | Ala | Lys 445 | Val | Met | Met | Asn | Leu 450 | Ser | His | Glu | Lys | Leu 455 | Val | Gln | |
| TTG | TAT | GGC | GTC | TGC | ACC | AAA | CAA | CGC | CCC | ATC | TTC | ATC | ATC | ACC | GAG | 1561 |
| Leu 460 | Tyr | Gly | Val | Cys | Thr 465 | Lys | Gln | Arg | Pro | Ile 470 | Phe | Ile | Ile | Thr | Glu 475 | |
| TAC | ATG | GCT | AAT | GGC | TGC | CTC | TTG | AAC | TAC | CTG | AGG | GAG | ATG | CGG | CAC | 1609 |
| Tyr | Met | Ala | Asn | Gly 480 | Cys | Leu | Leu | Asn | Tyr 485 | Leu | Arg | Glu | Met | Arg 490 | His | |
| CGC | TTC | CAG | ACA | CAG | CAG | CTG | CTT | GAG | ATG | TGC | AAA | GAT | GTC | TGT | GAA | 1657 |
| Arg | Phe | Gln | Thr | Gln 495 | Gln | Leu | Leu | Glu | Met 500 | Cys | Lys | Asp | Val | Cys 505 | Glu | |
| GCA | ATG | GAA | TAC | TTG | GAG | TCG | AAG | CAG | TTC | CTT | CAC | AGA | GAC | CTG | GCA | 1705 |
| Ala | Met | Glu | Tyr | Leu 510 | Glu | Ser | Lys | Gln | Phe 515 | Leu | His | Arg | Asp | Leu 520 | Ala | |
| GCT | CGA | AAC | TGT | TTG | GTA | AAC | GAT | CAA | GGA | GTT | GTG | AAA | GTA | TCT | GAC | 1753 |
| Ala | Arg | Asn 525 | Cys | Leu | Val | Asn | Asp 530 | Gln | Gly | Val | Val | Lys 535 | Val | Ser | Asp | |
| TTT | GGC | CTG | TCT | AGG | TAT | GTC | CTT | GAT | GAT | GAG | TAC | ACC | AGC | TCT | GTA | 1801 |
| Phe 540 | Gly | Leu | Ser | Arg | Tyr 545 | Val | Leu | Asp | Asp | Glu 550 | Tyr | Thr | Ser | Ser | Val 555 | |
| GGC | TCC | AAG | TTT | CCA | GTT | CGG | TGG | TCT | CCA | CCA | GAA | GTG | CTT | ATG | TAT | 1849 |
| Gly | Ser | Lys | Phe | Pro 560 | Val | Arg | Trp | Ser | Pro 565 | Pro | Glu | Val | Leu | Met 570 | Tyr | |
| AGC | AAG | TTC | AGC | AGC | AAA | TCT | GAC | ATC | TGG | GCT | TTT | GGG | GTT | TTA | ATG | 1897 |
| Ser | Lys | Phe | Ser 575 | Ser | Lys | Ser | Asp | Ile 580 | Trp | Ala | Phe | Gly | Val 585 | Leu | Met | |
| TGG | GAG | ATC | TAC | TCC | CTG | GGG | AAG | ATG | CCG | TAT | GAG | AGA | TTT | ACT | AAC | 1945 |
| Trp | Glu | Ile | Tyr | Ser 590 | Leu | Gly | Lys | Met | Pro 595 | Tyr | Glu | Arg | Phe | Thr 600 | Asn | |
| AGT | GAG | ACA | GCA | GAA | CAC | ATT | GCT | CAA | GGC | TTA | CGT | CTC | TAC | AGG | CCT | 1993 |
| Ser | Glu | Thr | Ala | Glu 605 | His | Ile | Ala | Gln | Gly 610 | Leu | Arg | Leu | Tyr | Arg 615 | Pro | |

```
CAT CTG GCA TCA GAG AGG GTA TAT ACC ATC ATG TAC AGC TGC TGG CAC           2041
His Leu Ala Ser Glu Arg Val Tyr Thr Ile Met Tyr Ser Cys Trp His
620             625                 630                 635

GAG AAA GCA GAT GAA CGT CCT AGT TTC AAA ATT CTC TTG AGT AAC ATT           2089
Glu Lys Ala Asp Glu Arg Pro Ser Phe Lys Ile Leu Leu Ser Asn Ile
                640                 645                 650

CTA GAT GTG ATG GAT GAA GAA TCC TGAGCTGGCT CCTAACCTCC GTGGATCTCC          2143
Leu Asp Val Met Asp Glu Glu Ser
            655                 660

TCCTCTCTCC TACAAAACCT AATTCCATGT TTCCTGAGGA GTTCCCTGGC TGCAGGGCTC         2203

TAGCTTCCAT GCGCCTACTG AATGCATCAA GAGCCCTGGA CATCTAGGAA TGCCTTTCTT         2263

CTCTCGTTCC CTGGCATACT GCTCTAAGCA AAGGTCAAGG GATTTCTGTG CCTAGTATTA         2323

CCCATAACTT CAAGACTCCA ACAGACTGAA TTGGGGATGG AACACTTTG GGGGAGGGAA          2383

AACTGTAAAT AGCTCACTAG TTGTCAACAG CTTGTTGTTA GTGTTAAGAG TGTGTGTGTG         2443

GGGGTAGGAA TGTGCATAAA TGGTGTTGTA ACTAATATGA AGAAAAAAAA AAAAAAAAA          2503

AA                                                                        2505
```

( 2 ) INFORMATION FOR SEQ ID NO:2:

( i ) SEQUENCE CHARACTERISTICS:
    ( A ) LENGTH: 659 amino acids
    ( B ) TYPE: amino acid
    ( D ) TOPOLOGY: linear ( i i ) MOLECULE TYPE: protein ( x i ) SEQUENCE DESCRIPTION: SEQ ID NO:2:

```
Met Ala Ala Val Ile Leu Glu Ser Ile Phe Leu Lys Arg Ser Gln Gln
 1               5                   10                  15

Lys Lys Lys Thr Ser Pro Leu Asn Phe Lys Lys Arg Leu Phe Leu Leu
                20                  25                  30

Thr Val His Lys Leu Ser Tyr Tyr Glu Tyr Asp Phe Glu Arg Gly Arg
            35                  40                  45

Arg Gly Ser Lys Lys Gly Ser Ile Asp Val Glu Lys Ile Thr Cys Val
    50                  55                  60

Glu Thr Val Ile Pro Glu Lys Asn Pro Pro Glu Arg Gln Ile Pro
65                  70                  75                  80

Arg Arg Gly Glu Glu Ser Ser Glu Met Glu Gln Ile Ser Ile Ile Glu
                85                  90                  95

Arg Phe Pro Tyr Pro Phe Gln Val Val Tyr Asp Glu Gly Pro Leu Tyr
                100                 105                 110

Val Phe Ser Pro Thr Glu Glu Leu Arg Lys Arg Trp Ile His Gln Leu
            115                 120                 125

Lys Asn Val Ile Arg Tyr Asn Ser Asp Leu Val Gln Lys Tyr His Pro
    130                 135                 140

Cys Phe Trp Ile Asp Gly Gln Tyr Leu Cys Cys Ser Gln Thr Ala Lys
145                 150                 155                 160

Asn Ala Met Gly Cys Gln Ile Leu Glu Asn Arg Asn Gly Ser Leu Lys
                165                 170                 175

Pro Gly Ser Ser His Arg Lys Thr Lys Lys Pro Leu Pro Pro Thr Pro
            180                 185                 190

Glu Glu Asp Gln Ile Leu Lys Lys Pro Leu Pro Pro Glu Pro Thr Ala
    195                 200                 205

Ala Pro Ile Ser Thr Thr Glu Leu Lys Lys Val Val Ala Leu Tyr Asp
210                 215                 220
```

```
Tyr Met Pro Met Asn Ala Asn Asp Leu Gln Leu Arg Lys Gly Glu Glu
225                 230                 235                 240
Tyr Phe Ile Leu Glu Glu Ser Asn Leu Pro Trp Trp Arg Ala Arg Asp
            245                 250                 255
Lys Asn Gly Gln Glu Gly Tyr Ile Pro Ser Asn Tyr Ile Thr Glu Ala
        260                 265                 270
Glu Asp Ser Ile Glu Met Tyr Glu Trp Tyr Ser Lys His Met Thr Arg
    275                 280                 285
Ser Gln Ala Glu Gln Leu Leu Lys Gln Glu Gly Lys Glu Gly Gly Phe
    290                 295                 300
Ile Val Arg Asp Ser Ser Lys Ala Gly Lys Tyr Thr Val Ser Val Phe
305                 310                 315                 320
Ala Lys Ser Thr Gly Glu Pro Gln Gly Val Ile Arg His Tyr Val Val
                325                 330                 335
Cys Ser Thr Pro Gln Ser Gln Tyr Tyr Leu Ala Glu Lys His Leu Phe
            340                 345                 350
Ser Thr Ile Pro Glu Leu Ile Asn Tyr His Gln His Asn Ser Ala Gly
        355                 360                 365
Leu Ile Ser Arg Leu Lys Tyr Pro Val Ser Lys Gln Asn Lys Asn Ala
    370                 375                 380
Pro Ser Thr Ala Gly Leu Gly Tyr Gly Ser Trp Glu Ile Asp Pro Lys
385                 390                 395                 400
Asp Leu Thr Phe Leu Lys Glu Leu Gly Thr Gly Gln Phe Gly Val Val
                405                 410                 415
Lys Tyr Gly Lys Trp Arg Gly Gln Tyr Asp Val Ala Ile Lys Met Ile
            420                 425                 430
Arg Glu Gly Ser Met Ser Glu Asp Glu Phe Ile Glu Glu Ala Lys Val
        435                 440                 445
Met Met Asn Leu Ser His Glu Lys Leu Val Gln Leu Tyr Gly Val Cys
    450                 455                 460
Thr Lys Gln Arg Pro Ile Phe Ile Ile Thr Glu Tyr Met Ala Asn Gly
465                 470                 475                 480
Cys Leu Leu Asn Tyr Leu Arg Glu Met Arg His Arg Phe Gln Thr Gln
                485                 490                 495
Gln Leu Leu Glu Met Cys Lys Asp Val Cys Glu Ala Met Glu Tyr Leu
            500                 505                 510
Glu Ser Lys Gln Phe Leu His Arg Asp Leu Ala Ala Arg Asn Cys Leu
        515                 520                 525
Val Asn Asp Gln Gly Val Val Lys Val Ser Asp Phe Gly Leu Ser Arg
530                 535                 540
Tyr Val Leu Asp Asp Glu Tyr Thr Ser Ser Val Gly Ser Lys Phe Pro
545                 550                 555                 560
Val Arg Trp Ser Pro Pro Glu Val Leu Met Tyr Ser Lys Phe Ser Ser
                565                 570                 575
Lys Ser Asp Ile Trp Ala Phe Gly Val Leu Met Trp Glu Ile Tyr Ser
            580                 585                 590
Leu Gly Lys Met Pro Tyr Glu Arg Phe Thr Asn Ser Glu Thr Ala Glu
        595                 600                 605
His Ile Ala Gln Gly Leu Arg Leu Tyr Arg Pro His Leu Ala Ser Glu
610                 615                 620
Arg Val Tyr Thr Ile Met Tyr Ser Cys Trp His Glu Lys Ala Asp Glu
625                 630                 635                 640
Arg Pro Ser Phe Lys Ile Leu Leu Ser Asn Ile Leu Asp Val Met Asp
```

| | 645 | | | | 650 | | | | 655 | | |
|---|---|---|---|---|---|---|---|---|---|---|---|

Glu Glu Ser ( 2 ) INFORMATION FOR SEQ ID NO:3:

( i ) SEQUENCE CHARACTERISTICS:
        ( A ) LENGTH: 625 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

| Met | Asn | Asn | Phe | Ile | Leu | Leu | Glu | Glu | Gln | Leu | Ile | Lys | Lys | Ser | Gln |
|---|---|---|---|---|---|---|---|---|---|---|---|---|---|---|---|
| 1 | | | | 5 | | | | | 10 | | | | | 15 | |
| Gln | Lys | Arg | Arg | Thr | Ser | Pro | Ser | Asn | Phe | Lys | Val | Arg | Phe | Phe | Val |
| | | | 20 | | | | | 25 | | | | | 30 | | |
| Leu | Thr | Lys | Ala | Ser | Leu | Ala | Tyr | Phe | Glu | Asp | Arg | His | Gly | Lys | Lys |
| | | 35 | | | | | 40 | | | | | 45 | | | |
| Arg | Thr | Leu | Lys | Gly | Ser | Ile | Glu | Leu | Ser | Arg | Ile | Lys | Cys | Val | Glu |
| | 50 | | | | | 55 | | | | | 60 | | | | |
| Ile | Val | Lys | Ser | Asp | Ile | Ser | Ile | Pro | Cys | His | Tyr | Lys | Tyr | Pro | Phe |
| 65 | | | | 70 | | | | | 75 | | | | | 80 | |
| Gln | Thr | Leu | Val | Tyr | Leu | Gln | Val | Val | His | Asp | Asn | Tyr | Leu | Leu | Tyr |
| | | | | 85 | | | | | 90 | | | | | 95 | |
| Val | Phe | Ala | Pro | Asp | Cys | Glu | Ser | Arg | Gln | Arg | Trp | Val | Leu | Thr | Leu |
| | | | 100 | | | | | 105 | | | | | 110 | | |
| Lys | Glu | Glu | Thr | Arg | Asn | Asn | Asn | Ser | Leu | Val | Ser | Lys | Tyr | His | Pro |
| | | | 115 | | | | | 120 | | | | | 125 | | |
| Asn | Phe | Trp | Met | Asp | Gly | Arg | Trp | Arg | Cys | Cys | Ser | Gln | Leu | Glu | Lys |
| | | 130 | | | | | 135 | | | | | 140 | | | |
| Pro | Ala | Val | Gly | Cys | Ala | Pro | Tyr | Asp | Pro | Ser | Lys | Asn | Ala | Ser | Lys |
| 145 | | | | | 150 | | | | | 155 | | | | | 160 |
| Lys | Pro | Leu | Pro | Pro | Thr | Pro | Glu | Asp | Asn | Arg | Arg | Ser | Phe | Gln | Glu |
| | | | | 165 | | | | | 170 | | | | | 175 | |
| Pro | Glu | Glu | Thr | Leu | Val | Ile | Ala | Leu | Tyr | Asp | Tyr | Gln | Thr | Asn | Asp |
| | | | 180 | | | | | 185 | | | | | 190 | | |
| Pro | Gln | Glu | Leu | Ala | Leu | Arg | Cys | Asp | Glu | Glu | Tyr | Tyr | Leu | Leu | Asp |
| | | 195 | | | | | 200 | | | | | 205 | | | |
| Ser | Ser | Glu | Ile | His | Trp | Trp | Arg | Val | Gln | Asp | Lys | Asn | Gly | His | Glu |
| 210 | | | | | 215 | | | | | 220 | | | | | |
| Gly | Tyr | Ala | Pro | Ser | Ser | Tyr | Leu | Val | Glu | Lys | Ser | Pro | Asn | Asn | Leu |
| 225 | | | | | 230 | | | | | 235 | | | | | 240 |
| Glu | Thr | Tyr | Glu | Trp | Tyr | Asn | Lys | Ser | Ile | Ser | Arg | Asp | Lys | Ala | Glu |
| | | | | 245 | | | | | 250 | | | | | 255 | |
| Lys | Leu | Leu | Leu | Asp | Thr | Gly | Lys | Glu | Gly | Ala | Phe | Met | Val | Arg | Asp |
| | | | 260 | | | | | 265 | | | | | 270 | | |
| Ser | Arg | Thr | Pro | Gly | Thr | Tyr | Thr | Val | Ser | Val | Phe | Thr | Lys | Ala | Ile |
| | | 275 | | | | | 280 | | | | | 285 | | | |
| Ile | Ser | Glu | Asn | Pro | Cys | Ile | Lys | His | Tyr | His | Ile | Lys | Glu | Thr | Asn |
| | 290 | | | | | 295 | | | | | 300 | | | | |
| Asp | Ser | Pro | Lys | Arg | Tyr | Tyr | Val | Ala | Glu | Lys | Tyr | Val | Phe | Asp | Ser |
| 305 | | | | | 310 | | | | | 315 | | | | | 320 |
| Ile | Pro | Leu | Leu | Ile | Gln | Tyr | His | Gln | Tyr | Asn | Gly | Gly | Gly | Leu | Val |
| | | | | 325 | | | | | 330 | | | | | 335 | |

```
Thr  Arg  Leu  Arg  Tyr  Pro  Val  Cys  Ser  Trp  Arg  Gln  Lys  Ala  Val  Pro
               340                 345                      350

Thr  Ala  Gly  Leu  Arg  Tyr  Gly  Lys  Trp  Val  Ile  Gln  Pro  Ser  Glu  Leu
               355                 360                      365

Thr  Phe  Val  Gln  Glu  Ile  Gly  Ser  Gly  Gln  Phe  Gly  Leu  Val  His  Leu
     370                      375                      380

Gly  Tyr  Trp  Leu  Asn  Lys  Asp  Lys  Val  Ala  Ile  Lys  Thr  Ile  Gln  Glu
385                      390                 395                           400

Gly  Ala  Met  Ser  Glu  Glu  Asp  Phe  Ile  Glu  Ala  Glu  Val  Met  Met
                    405                      410                      415

Lys  Leu  Ser  His  Pro  Lys  Leu  Val  Gln  Leu  Tyr  Gly  Val  Cys  Leu  Glu
               420                      425                 430

Gln  Ala  Pro  Ile  Cys  Leu  Val  Phe  Glu  Phe  Met  Glu  His  Gly  Cys  Leu
          435                      440                      445

Ser  Asp  Tyr  Leu  Arg  Ser  Gln  Arg  Gly  Leu  Phe  Ala  Ala  Glu  Thr  Leu
     450                      455                 460

Leu  Gly  Met  Cys  Leu  Asp  Val  Cys  Glu  Gly  Met  Ala  Tyr  Leu  Glu  Lys
465                      470                 475                           480

Ala  Cys  Val  Ile  His  Arg  Asp  Leu  Ala  Ala  Arg  Asn  Cys  Leu  Val  Gly
               485                      490                      495

Glu  Asn  Gln  Val  Ile  Lys  Val  Ser  Asp  Phe  Gly  Met  Thr  Arg  Phe  Val
               500                 505                      510

Leu  Asp  Asp  Gln  Tyr  Thr  Ser  Ser  Thr  Gly  Thr  Lys  Phe  Pro  Val  Lys
          515                      520                      525

Trp  Ala  Ser  Pro  Glu  Val  Phe  Ser  Phe  Ser  Arg  Tyr  Ser  Ser  Lys  Ser
     530                      535                      540

Asp  Val  Trp  Ser  Phe  Gly  Val  Leu  Met  Trp  Glu  Val  Phe  Ser  Glu  Gly
545                      550                      555                      560

Lys  Ile  Pro  Tyr  Glu  Asn  Arg  Ser  Asn  Ser  Glu  Val  Val  Glu  Asp  Ile
                    565                      570                      575

Ser  Thr  Gly  Phe  Arg  Leu  Tyr  Lys  Pro  Arg  Leu  Ala  Ser  Cys  His  Val
               580                      585                 590

Tyr  Gln  Ile  Met  Asn  His  Cys  Trp  Lys  Glu  Lys  Pro  Glu  Asp  Arg  Pro
          595                      600                      605

Pro  Phe  Ser  Gln  Leu  Leu  Ser  Gln  Leu  Ala  Glu  Ile  Ala  Glu  Ala  Gly
     610                      615                      620

Leu
625
```

( 2 ) INFORMATION FOR SEQ ID NO:4:

( i ) SEQUENCE CHARACTERISTICS:
        ( A ) LENGTH: 599 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

```
Met  Asn  Phe  Asn  Thr  Ile  Leu  Glu  Glu  Ile  Leu  Ile  Lys  Arg  Ser  Gln
1                 5                      10                      15

Gln  Lys  Lys  Lys  Thr  Ser  Leu  Leu  Asn  Phe  Lys  Glu  Arg  Leu  Cys  Val
               20                      25                      30

Leu  Pro  Lys  Ser  Val  Leu  Ser  Tyr  Tyr  Glu  Tyr  Phe  Gly  Arg  Ala  Glu
               35                      40                 45

Lys  Lys  Tyr  Arg  Lys  Gly  Val  Ile  Asp  Ile  Ser  Lys  Ile  Lys  Cys  Val
```

|   |   |   | 50 |   |   |   |   | 55 |   |   |   |   | 60 |   |   |
|---|---|---|---|---|---|---|---|---|---|---|---|---|---|---|---|
| Glu | Ile | Val | Lys | Asn | Asp | Asp | Gly | Val | Ile | Pro | Cys | Gln | Asn | Phe | Lys |
| 65 |   |   |   |   | 70 |   |   |   | 75 |   |   |   |   |   | 80 |
| Pro | Phe | Gln | Val | Val | His | Asp | Ala | Asn | Thr | Leu | Tyr | Ile | Phe | Ala | Pro |
|   |   |   |   | 85 |   |   |   |   | 90 |   |   |   |   | 95 |   |
| Ser | Pro | Ser | Arg | Asp | Arg | Trp | Val | Lys | Lys | Leu | Lys | Glu | Glu | Ile | Lys |
|   |   |   | 100 |   |   |   |   | 105 |   |   |   |   | 110 |   |   |
| Asn | Asn | Asn | Asn | Ile | Met | Ile | Lys | Tyr | His | Pro | Lys | Phe | Trp | Ala | Asp |
|   |   |   | 115 |   |   |   | 120 |   |   |   |   | 125 |   |   |   |
| Gly | Ser | Tyr | Gln | Cys | Cys | Arg | Gln | Thr | Glu | Lys | Leu | Ala | Pro | Gly | Cys |
|   | 130 |   |   |   |   | 135 |   |   |   |   | 140 |   |   |   |   |
| Glu | Lys | Tyr | Asn | Leu | Phe | Glu | Ser | Ser | Ile | Arg | Lys | Thr | Leu | Pro | Pro |
| 145 |   |   |   |   | 150 |   |   |   |   | 155 |   |   |   |   | 160 |
| Ala | Pro | Glu | Ile | Lys | Lys | Arg | Arg | Pro | Pro | Pro | Pro | Ile | Pro | Pro | Glu |
|   |   |   |   | 165 |   |   |   |   | 170 |   |   |   |   | 175 |   |
| Glu | Glu | Asn | Thr | Glu | Glu | Ile | Val | Val | Ala | Met | Tyr | Asp | Phe | Gln | Ala |
|   |   |   | 180 |   |   |   |   | 185 |   |   |   |   | 190 |   |   |
| Thr | Glu | Ala | His | Asp | Leu | Gln | Leu | Glu | Lys | Gly | Gln | Tyr | Ile | Ile | Leu |
|   |   | 195 |   |   |   |   | 200 |   |   |   |   | 205 |   |   |   |
| Glu | Lys | Asn | Asp | Leu | His | Trp | Trp | Arg | Ala | Arg | Asp | Tyr | Asn | Trp | Tyr |
|   | 210 |   |   |   |   | 215 |   |   |   |   | 220 |   |   |   |   |
| Cys | Arg | Asn | Thr | Asn | Arg | Ser | Lys | Ala | Glu | Gln | Leu | Leu | Arg | Thr | Glu |
| 225 |   |   |   |   | 230 |   |   |   |   | 235 |   |   |   |   | 240 |
| Asp | Lys | Glu | Gly | Gly | Phe | Met | Val | Arg | Asp | Ser | Ser | Gln | Pro | Gly | Leu |
|   |   |   |   | 245 |   |   |   |   | 250 |   |   |   |   | 255 |   |
| Tyr | Thr | Val | Ser | Leu | Tyr | Thr | Lys | Phe | Gly | Gly | Glu | Gly | Ser | Ser | Gly |
|   |   |   | 260 |   |   |   |   | 265 |   |   |   |   | 270 |   |   |
| Phe | Arg | His | Tyr | His | Ile | Leu | Glu | Thr | Ala | Thr | Ser | Pro | Tyr | Tyr | Leu |
|   |   | 275 |   |   |   |   | 280 |   |   |   |   | 285 |   |   |   |
| Ala | Glu | Lys | His | Ala | Phe | Gly | Ser | Ile | Pro | Glu | Ile | Ile | Glu | Tyr | His |
|   | 290 |   |   |   |   | 295 |   |   |   |   | 300 |   |   |   |   |
| Lys | His | Asn | Ala | Ala | Gly | Leu | Val | Thr | Arg | Leu | Arg | Tyr | Pro | Val | Ser |
| 305 |   |   |   |   | 310 |   |   |   |   | 315 |   |   |   |   | 320 |
| Thr | Lys | Gln | Lys | Asn | Ala | Pro | Thr | Thr | Ala | Gly | Phe | Ser | Tyr | Asp | Lys |
|   |   |   |   | 325 |   |   |   |   | 330 |   |   |   |   | 335 |   |
| Trp | Glu | Ile | Asn | Pro | Ser | Glu | Leu | Thr | Phe | Met | Arg | Glu | Leu | Gly | Ser |
|   |   |   | 340 |   |   |   |   | 345 |   |   |   |   | 350 |   |   |
| Gly | Leu | Phe | Gly | Val | Val | Arg | Leu | Gly | Lys | Trp | Arg | Ala | Gln | Tyr | Lys |
|   |   | 355 |   |   |   |   | 360 |   |   |   |   | 365 |   |   |   |
| Val | Ala | Ile | Lys | Ala | Ile | Arg | Glu | Gly | Ala | Met | Cys | Glu | Glu | Asp | Phe |
|   | 370 |   |   |   |   | 375 |   |   |   |   | 380 |   |   |   |   |
| Ile | Glu | Glu | Ala | Lys | Val | Met | Met | Lys | Leu | Thr | His | Pro | Lys | Leu | Val |
| 385 |   |   |   |   | 390 |   |   |   |   | 395 |   |   |   |   | 400 |
| Gln | Leu | Tyr | Gly | Val | Cys | Thr | Gln | Gln | Lys | Pro | Ile | Tyr | Ile | Val | Thr |
|   |   |   |   | 405 |   |   |   |   | 410 |   |   |   |   | 415 |   |
| Glu | Phe | Met | Glu | Arg | Gly | Cys | Leu | Leu | Asn | Phe | Leu | Arg | Gln | Arg | Gln |
|   |   |   | 420 |   |   |   |   | 425 |   |   |   |   | 430 |   |   |
| Gly | His | Phe | Ser | Arg | Arg | Met | Leu | Leu | Ser | Met | Cys | Gln | Arg | Val | Cys |
|   |   | 435 |   |   |   |   | 440 |   |   |   |   | 445 |   |   |   |
| Glu | Gly | Met | Glu | Tyr | Leu | Glu | Arg | Asn | Ser | Phe | Ile | His | Arg | Asp | Leu |
|   | 450 |   |   |   |   | 455 |   |   |   |   | 460 |   |   |   |   |
| Ala | Ala | Arg | Asn | Cys | Leu | Val | Asn | Glu | Ala | Gly | Val | Val | Lys | Val | Ser |
| 465 |   |   |   |   | 470 |   |   |   |   | 475 |   |   |   |   | 480 |

|     |     |     |     |     |     |     |     |     |     |     |     |     |     |     |     |
| --- | --- | --- | --- | --- | --- | --- | --- | --- | --- | --- | --- | --- | --- | --- | --- |
| Asp | Phe | Gly | Met | Ala<br>485 | Arg | Tyr | Val | Leu | Asp<br>490 | Asp | Gln | Tyr | Thr | Ser<br>495 | Ser |
| Ser | Gly | Ala | Lys<br>500 | Phe | Pro | Val | Lys<br>505 | Trp | Cys | Pro | Pro | Glu | Val<br>510 | Phe | Asn |
| Tyr | Ser | Arg<br>515 | Phe | Ser | Ser | Lys | Ser<br>520 | Asp | Val | Trp | Ser | Phe<br>525 | Gly | Val | Leu |
| Met | Trp<br>530 | Glu | Ile | Phe | Thr | Glu<br>535 | Gly | Arg | Met | Pro | Phe<br>540 | Glu | Lys | Asn | Thr |
| Asn<br>545 | Tyr | Glu | Val | Val | Thr<br>550 | Met | Val | Thr | Arg | Gly<br>555 | His | Arg | Leu | Gly | Arg<br>560 |
| Pro | Lys | Leu | Ala | Thr<br>565 | Lys | Tyr | Leu | Tyr | Glu<br>570 | Val | Met | Leu | Arg | Cys<br>575 | Trp |
| Gln | Glu | Glu | Ser<br>580 | Cys | Leu | Cys | Arg | Val<br>585 | Ala | Gln | Asp | Leu | Ser<br>590 | Ser | Lys |
| Asn | Leu | Ile<br>595 | Gly | Ser | Arg | Phe |     |     |     |     |     |     |     |     |     |

( 2 ) INFORMATION FOR SEQ ID NO:5:

( i ) SEQUENCE CHARACTERISTICS:
        ( A ) LENGTH: 588 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

|     |     |     |     |     |     |     |     |     |     |     |     |     |     |     |     |
| --- | --- | --- | --- | --- | --- | --- | --- | --- | --- | --- | --- | --- | --- | --- | --- |
| Met<br>1 | Lys | Glu | Arg | Val<br>5 | Lys | Glu | Met | Lys | Val<br>10 | Phe | Gly | Cys | Arg | Leu<br>15 | Asn |
| Phe | Trp | Asn | His<br>20 | Ile | Gly | His | Glu | Pro<br>25 | Asp | Gln | Phe | Gln | Asn<br>30 | Gln | Arg |
| Arg | Gln | Arg<br>35 | Arg | Val | Leu | Gln | Pro<br>40 | Arg | Ile | Gln | Arg | Ala<br>45 | Ala | Val | Ser |
| Pro | Asn<br>50 | Ser | Ser | Thr | Thr | Asn<br>55 | Ser | Gln | Phe | Ser | Leu<br>60 | Gln | His | Asn | Ser |
| Ser<br>65 | Gly | Ser | Leu | Gly | Gly<br>70 | Gly | Val | Gly | Gly | Gly<br>75 | Leu | Gly | Gly | Gly | Gly<br>80 |
| Ser | Leu | Gly | Leu | Gly<br>85 | Gly | Gly | Gly | Gly | Gly<br>90 | Gly | Gly | Ser | Cys | Thr<br>95 | Pro |
| Thr | Ser | Leu | Gln<br>100 | Pro | Gln | Ser | Ser | Leu<br>105 | Thr | Thr | Phe | Lys | Gln<br>110 | Ser | Pro |
| Thr | Leu | Leu | Asn<br>115 | Gly | Asn | Gly | Asn<br>120 | Leu | Leu | Asp | Ala | Met<br>125 | Pro | Gly |
| Gly | Ile<br>130 | Pro | Thr | Pro | Gly | Thr<br>135 | Pro | Asn | Ser | Lys | Ala<br>140 | Lys | Asp | Asn | Ser |
| His<br>145 | Phe | Val | Lys | Leu | Val<br>150 | Val | Ala | Leu | Tyr | Leu<br>155 | Gly | Lys | Ala | Ile | Glu<br>160 |
| Gly | Gly | Asp | Leu | Ser<br>165 | Val | Gly | Glu | Lys | Asn<br>170 | Ala | Glu | Tyr | Glu | Val<br>175 | Ile |
| Asp | Asp | Ser | Gln<br>180 | Glu | His | Trp | Trp | Lys<br>185 | Val | Lys | Asp | Ala | Leu<br>190 | Gly | Asn |
| Val | Gly | Tyr<br>195 | Ile | Pro | Ser | Asn | Tyr<br>200 | Val | Gln | Ala | Glu | Ala<br>205 | Leu | Leu | Gly |
| Leu | Glu<br>210 | Arg | Tyr | Glu | Trp | Tyr<br>215 | Val | Gly | Tyr | Met | Ser<br>220 | Arg | Gln | Arg | Ala |
| Glu | Ser | Leu | Leu | Lys | Gln | Gly | Asp | Lys | Glu | Gly | Cys | Phe | Val | Val | Arg |

|     |     |     |     | 225 |     |     |     |     | 230 |     |     |     |     | 235 |     |     |     |     | 240 |
| --- | --- | --- | --- | --- | --- | --- | --- | --- | --- | --- | --- | --- | --- | --- | --- | --- | --- | --- | --- |
| Lys | Ser | Ser | Thr | Lys<br>245 | Gly | Leu | Tyr | Thr | Leu<br>250 | Ser | Leu | His | Thr | Lys<br>255 | Val |
| Pro | Gln | Ser | His<br>260 | Val | Lys | His | Tyr | His<br>265 | Ile | Lys | Gln | Asn | Ala<br>270 | Arg | Cys |
| Glu | Tyr | Tyr<br>275 | Leu | Ser | Glu | Lys | His<br>280 | Cys | Cys | Glu | Thr | Ile<br>285 | Pro | Asp | Leu |
| Ile | Asn<br>290 | Tyr | His | Arg | His | Asn<br>295 | Ser | Gly | Gly | Leu | Ala<br>300 | Cys | Arg | Leu | Lys |
| Ser<br>305 | Ser | Pro | Cys | Asp | Arg<br>310 | Pro | Val | Pro | Pro | Thr<br>315 | Ala | Gly | Leu | Ser | His<br>320 |
| Asp | Lys | Trp | Glu | Ile<br>325 | His | Pro | Ile | Gln | Leu<br>330 | Met | Leu | Met | Glu | Glu<br>335 | Leu |
| Gly | Ser | Gly | Gln<br>340 | Phe | Gly | Val | Val | Arg<br>345 | Arg | Gly | Lys | Trp | Arg<br>350 | Gly | Ser |
| Ile | Asp | Thr<br>355 | Ala | Val | Lys | Met | Met<br>360 | Lys | Glu | Gly | Thr | Met<br>365 | Ser | Glu | Asp |
| Asp | Phe<br>370 | Ile | Glu | Glu | Ala | Lys<br>375 | Val | Met | Thr | Lys | Leu<br>380 | Gln | His | Pro | Asn |
| Leu<br>385 | Val | Gln | Leu | Tyr | Gly<br>390 | Val | Cys | Thr | Lys | His<br>395 | Arg | Pro | Ile | Tyr | Ile<br>400 |
| Val | Thr | Glu | Tyr | Met<br>405 | Lys | His | Gly | Ser | Leu<br>410 | Leu | Asn | Tyr | Leu | Arg<br>415 | Arg |
| His | Glu | Lys | Thr<br>420 | Leu | Ile | Gly | Asn | Met<br>425 | Gly | Leu | Leu | Leu | Asp<br>430 | Met | Cys |
| Ile | Gln | Val<br>435 | Ser | Lys | Gly | Met | Thr<br>440 | Tyr | Leu | Glu | Arg | His<br>445 | Asn | Tyr | Ile |
| His | Arg<br>450 | Asp | Leu | Ala | Ala | Arg<br>455 | Asn | Cys | Leu | Val | Gly<br>460 | Ser | Glu | Asn | Val |
| Val<br>465 | Lys | Val | Ala | Asp | Phe<br>470 | Gly | Leu | Ala | Arg | Tyr<br>475 | Val | Leu | Asp | Asp | Gln<br>480 |
| Tyr | Thr | Ser | Ser | Gly<br>485 | Gly | Thr | Lys | Phe | Pro<br>490 | Ile | Lys | Trp | Ala | Pro<br>495 | Pro |
| Glu | Val | Leu | Asn<br>500 | Tyr | Thr | Arg | Phe | Ser<br>505 | Ser | Lys | Ser | Asp | Val<br>510 | Trp | Ala |
| Tyr | Gly | Val<br>515 | Leu | Met | Trp | Glu | Ile<br>520 | Phe | Thr | Cys | Gly | Lys<br>525 | Met | Pro | Tyr |
| Gly | Arg<br>530 | Leu | Lys | Asn | Thr | Glu<br>535 | Val | Val | Glu | Arg | Val<br>540 | Gln | Arg | Gly | Ile |
| Ile<br>545 | Leu | Glu | Lys | Pro | Lys<br>550 | Ser | Cys | Ala | Lys | Glu<br>555 | Ile | Tyr | Asp | Val | Met<br>560 |
| Lys | Leu | Cys | Trp | Ser<br>565 | His | Gly | Pro | Glu | Glu<br>570 | Arg | Pro | Ala | Phe | Arg<br>575 | Val |
| Leu | Met | Asp | Gln<br>580 | Leu | Ala | Leu | Val | Ala<br>585 | Gln | Thr | Leu | | | | |

( 2 ) INFORMATION FOR SEQ ID NO:6:

( i ) SEQUENCE CHARACTERISTICS:
        ( A ) LENGTH: 442 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

| | | | | | | | | | | | | | | |
|---|---|---|---|---|---|---|---|---|---|---|---|---|---|---|
| Met<br>1 | Ala | Ala | Val | Ile<br>5 | Leu | Glu | Ser | Ile | Phe<br>10 | Leu | Lys | Arg | Ser | Gln<br>15 | Gln |
| Lys | Lys | Lys | Arg<br>20 | Ser | Pro | Leu | Asn | Phe<br>25 | Lys | Lys | Arg | Leu | Phe<br>30 | Leu | Leu |
| Thr | Val | His<br>35 | Lys | Leu | Ser | Tyr | Tyr<br>40 | Glu | Tyr | Asp | Phe | Glu<br>45 | Arg | Gly | Arg |
| Arg | Gly<br>50 | Ser | Lys | Lys | Gly | Ser<br>55 | Ile | Asp | Val | Glu | Lys<br>60 | Ile | Thr | Cys | Val |
| Glu<br>65 | Thr | Val | Val | Pro | Glu<br>70 | Lys | Asn | Pro | Pro | Glu<br>75 | Arg | Gln | Ile | Pro<br>80 |
| Arg | Arg | Gly | Glu | Glu<br>85 | Ser | Ser | Glu | Met | Glu<br>90 | Gln | Ile | Ser | Ile | Ile<br>95 | Glu |
| Arg | Phe | Pro | Tyr<br>100 | Pro | Phe | Gln | Val | Val<br>105 | Tyr | Asp | Glu | Gly | Pro<br>110 | Leu | Tyr |
| Val | Phe | Ser<br>115 | Pro | Thr | Glu | Glu | Leu<br>120 | Arg | Lys | Arg | Trp | Ile<br>125 | His | Gln | Leu |
| Lys | Asn<br>130 | Val | Ile | Arg | Tyr | Asn<br>135 | Ser | Asp | Leu | Val | Gln<br>140 | Lys | Tyr | His | Pro |
| Cys<br>145 | Phe | Trp | Ile | Asp | Gly<br>150 | Gln | Tyr | Leu | Cys | Cys<br>155 | Ser | Gln | Thr | Ala | Lys<br>160 |
| Asn | Ala | Met | Gly | Cys<br>165 | Gln | Ile | Leu | Glu | Asn<br>170 | Arg | Asn | Gly | Ser | Leu<br>175 | Lys |
| Pro | Gly | Ser | Ser<br>180 | His | Arg | Lys | Thr | Lys<br>185 | Lys | Pro | Leu | Pro | Pro<br>190 | Thr | Pro |
| Glu | Glu | Asp<br>195 | Gln | Ile | Leu | Lys | Lys<br>200 | Pro | Leu | Pro | Pro | Glu<br>205 | Pro | Ala | Ala |
| Ala | Pro<br>210 | Val | Ser | Thr | Ser | Glu<br>215 | Leu | Lys | Lys | Val | Ala<br>220 | Leu | Tyr | Asp |
| Tyr<br>225 | Met | Pro | Met | Asn | Ala<br>230 | Asn | Asp | Leu | Gln | Leu<br>235 | Arg | Lys | Gly | Asp | Glu<br>240 |
| Tyr | Phe | Ile | Leu | Glu<br>245 | Glu | Ser | Asn | Leu | Pro<br>250 | Trp | Trp | Arg | Ala | Arg | Asp<br>255 |
| Lys | Asn | Gly | Gln | Glu<br>260 | Gly | Tyr | Ile | Pro | Ser<br>265 | Asn | Asp | Val | Thr | Glu<br>270 | Ala |
| Glu | Asp | Ser<br>275 | Ile | Glu | Met | Tyr | Glu<br>280 | Trp | Tyr | Ser | Lys | His<br>285 | Met | Thr | Arg |
| Ser | Gln<br>290 | Ala | Glu | Gln | Leu | Leu<br>295 | Lys | Gln | Glu | Gly | Lys<br>300 | Glu | Gly | Gly | Phe |
| Ile<br>305 | Val | Arg | Asp | Ser | Ser<br>310 | Lys | Ala | Ala | Lys | Tyr<br>315 | Thr | Leu | Ser | Val | Phe<br>320 |
| Ala | Lys | Ser | Thr | Gly<br>325 | Asp | Pro | Gln | Gly | Val<br>330 | Ile | Arg | His | Tyr | Val<br>335 | Val |
| Cys | Ser | Thr | Pro<br>340 | Gln | Ser | Gln | Tyr | Tyr<br>345 | Leu | Ala | Glu | Lys | His<br>350 | Leu | Phe |
| Ser | Thr | Ile<br>355 | Pro | Glu | Leu | Ile | Asn<br>360 | Tyr | His | Gln | His | Asn<br>365 | Ser | Ala | Gly |
| Leu | Ile<br>370 | Ser | Arg | Leu | Lys | Tyr<br>375 | Pro | Val | Ser | Gln | Gln<br>380 | Asn | Lys | Asn | Ala |
| Pro<br>385 | Ser | Thr | Ala | Gly | Leu<br>390 | Gly | Tyr | Gly | Ser | Trp<br>395 | Glu | Ile | Asp | Pro | Lys<br>400 |
| Asp | Leu | Thr | Phe | Leu<br>405 | Lys | Glu | Leu | Gly | Thr<br>410 | Gly | Gln | Phe | Gly | Val<br>415 | Val |
| Lys | Tyr | Gly | Lys | Trp | Arg | Gly | Gln | Tyr | Asp | Val | Ala | Ile | Lys | Met | Ile |

|  | 420 | 425 | 430 |
| --- | --- | --- | --- |

Lys Glu Gly Ser Met Ser Glu Asp Glu Phe
435                               440

( 2 ) INFORMATION FOR SEQ ID NO:7:

( i ) SEQUENCE CHARACTERISTICS:
        ( A ) LENGTH: 1418 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:7:

| ACCTTCCAAG | TCCTGGCATC | TCAATGCATC | TGGGAAGCTA | CCTGCATTAA | GTCAGGACTG | 60 |
| --- | --- | --- | --- | --- | --- | --- |
| AGCACACAGG | TGAACTCCAG | AAAGAAGAAG | CTATGGCCGC | AGTGATTCTG | GAGAGCATCT | 120 |
| TTCTGAAGCG | ATCCCAACAG | AAAAAGAAAA | GATCACCTCT | AAACTTCAAG | AAGCGCCTGT | 180 |
| TTCTCTTGAC | CGTGCACAAA | CTCTCCTACT | ATGAGTATGA | CTTTGAACGT | GGGAGAAGAG | 240 |
| GCAGTAAGAA | GGGTTCAATA | GATGTTGAGA | AGATCACTTG | TGTTGAAACA | GTGGTTCCTG | 300 |
| AAAAAAATCC | TCCTCCAGAA | AGACAGATTC | CGAGAAGAGG | TGAAGAGTCC | AGTGAAATGG | 360 |
| AGCAAATTTC | AATCATTGAA | AGGTTCCCTT | ATCCCTTCCA | GGTTGTATAT | GATGAAGGGC | 420 |
| CTCTCTACGT | CTTCTCCCCA | ACTGAAGAAC | TAAGGAAGCG | GTGGATTCAC | CAGCTCAAAA | 480 |
| ACGTAATCCG | GTACAACAGT | GATCTGGTTC | AGAAATATCA | CCCTTGCTTC | TGGATCGATG | 540 |
| GGCAGTATCT | CTGCTGCTCT | CAGACAGCCA | AAAATGCTAT | GGGCTGCCAA | ATTTTGGAGA | 600 |
| ACAGGAATGG | AAGCTTAAAA | CCTGGGAGTT | CTCACCGGAA | GACAAAAAAG | CCTCTTCCCC | 660 |
| CAACGCCTGA | GGAGGACCAG | ATCTTGAAAA | AGCCACTACC | GCCTGAGCCA | GCAGCAGCAC | 720 |
| CAGTCTCCAC | AAGTGAGCTG | AAAAAGGAAG | TGGCCCTTTA | TGATTACATG | CCAATGAATG | 780 |
| CAAATGATCT | ACAGCTGCGG | AAGGGTGATG | AATATTTTAT | CTTGGAGGAA | AGCAACTTAC | 840 |
| CATGGTGGAG | AGCACGAGAT | AAAAATGGGC | AGGAAGGCTA | CATTCCTAGT | AACGATGTCA | 900 |
| CTGAAGCAGA | AGACTCCATA | GAAATGTATG | AGTGGTATTC | CAAACACATG | ACTCGGAGTC | 960 |
| AGGCTGAGCA | ACTGCTAAAG | CAAGAGGGGA | AAGAAGGAGG | TTTCATTGTC | AGAGACTCCA | 1020 |
| GCAAAGCTGC | AAAATATACA | CTGTCTGTGT | TTGCTAAATC | CACAGGGGAC | CCTCAAGGGG | 1080 |
| TGATACGTCA | TTATGTTGTG | TGTTCCACAC | CTCAGAGCCA | GTATTACCTG | GCTGAGAAGC | 1140 |
| ACCTTTTCAG | CACCATCCCT | GAGCTCATTA | ACTACCATCA | GCACAACTCT | GCAGGACTCA | 1200 |
| TATCCAGGCT | CAAATATCCA | GTGTCTCAAC | AAAACAAGAA | TGCACCTTCC | ACTGCAGGCC | 1260 |
| TGGGATACGG | ATCATGGGAA | ATTGATCCAA | AGGACCTGAC | CTTCTTGAAG | GAGCTGGGGA | 1320 |
| CTGGACAATT | TGGGGTAGTG | AAGTATGGGA | AATGGAGAGG | CCAGTACGAC | GTGGCCATCA | 1380 |
| AGATGATCAA | AGAAGGCTCC | ATGTCTGAAG | ATGAATTC |  |  | 1418 |